(12) United States Patent
Warkentin

(10) Patent No.: US 10,588,996 B2
(45) Date of Patent: Mar. 17, 2020

(54) VENT BALLOON

(71) Applicant: William Paul Warkentin, West Bloomfield, MI (US)

(72) Inventor: William Paul Warkentin, West Bloomfield, MI (US)

( * ) Notice: Subject to any disclaimer, the term of this patent is extended or adjusted under 35 U.S.C. 154(b) by 0 days.

(21) Appl. No.: 16/431,864

(22) Filed: Jun. 5, 2019

(65) Prior Publication Data

US 2019/0282721 A1    Sep. 19, 2019

Related U.S. Application Data

(63) Continuation-in-part of application No. PCT/US2018/031545, filed on May 8, 2018, which is a continuation-in-part of application No. 15/853,093, filed on Dec. 22, 2017.

(60) Provisional application No. 62/504,839, filed on May 11, 2017.

(51) Int. Cl.
| | |
|---|---|
| *A61L 9/12* | (2006.01) |
| *A63H 27/10* | (2006.01) |
| *A63H 33/40* | (2006.01) |
| *A63H 3/06* | (2006.01) |

(52) U.S. Cl.
CPC ............... *A61L 9/122* (2013.01); *A63H 3/06* (2013.01); *A63H 27/10* (2013.01); *A63H 33/40* (2013.01)

(58) Field of Classification Search
CPC .. A63H 3/06; A63H 27/10; A63H 2027/1008; A63H 2027/1025; A63H 2027/1033; A63H 2027/1058; A63H 2027/1075; A63H 33/00; A63H 33/40; A63H 33/42; G09F 19/00; G09F 19/18; A61L 9/122
See application file for complete search history.

(56) References Cited

U.S. PATENT DOCUMENTS

| | | | |
|---|---|---|---|
| 1,824,388 A | 9/1931 | Birch | |
| 3,149,017 A | 9/1964 | Ehrreich et al. | |
| 4,765,079 A * | 8/1988 | Takahashi | ............... G09F 19/00 40/412 |
| 4,920,674 A | 5/1990 | Shaeffer | |

(Continued)

FOREIGN PATENT DOCUMENTS

| | | |
|---|---|---|
| JP | 2002-287677 | 10/2002 |
| JP | 2008-299300 | 12/2008 |

(Continued)

*Primary Examiner* — Eugene L Kim
*Assistant Examiner* — Alyssa M Hylinski
(74) *Attorney, Agent, or Firm* — Kenneth I. Kohn

(57) ABSTRACT

A vent balloon, including an inflatable body operatively attached to a molded plastic base on a proximal side, wherein the inflatable body is inflated by a mechanism of an air vent or a fan operatively attached to the molded plastic base, and including a scent mechanism operatively attached to the molded plastic base for dispersing scent in a room that relates to a design on the inflatable body. A method of using a vent balloon by flowing air through an inflatable body of a vent balloon through a molded plastic base, wherein the air comes from a source of an air vent or a fan operatively attached to the molded plastic base, inflating the inflatable body, and flowing air over at least one scent mechanism operatively attached to the molded plastic base that relates to a design on the inflatable body and releasing scent into the air.

16 Claims, 34 Drawing Sheets

(56) References Cited

U.S. PATENT DOCUMENTS

| | | | | |
|---|---|---|---|---|
| 5,016,848 | A | * | 5/1991 | Metz ..................... A63H 27/10 248/176.1 |
| 5,186,675 | A | * | 2/1993 | D Stoddard ............. A63H 3/06 40/212 |
| 5,778,581 | A | | 7/1998 | Bailey |
| 6,148,551 | A | | 11/2000 | Glass |
| 6,428,185 | B1 | * | 8/2002 | Lin ........................ F21V 1/06 362/253 |
| 6,786,793 | B1 | * | 9/2004 | Wang ..................... A63H 3/06 40/412 |
| 6,804,905 | B1 | | 10/2004 | Burger, III et al. |
| 7,356,951 | B2 | * | 4/2008 | Spielberger ......... G09F 15/0025 40/412 |
| 7,381,112 | B1 | | 6/2008 | Symes |
| 7,686,668 | B1 | | 3/2010 | Butler |
| 7,981,470 | B1 | | 7/2011 | Butler |
| 8,919,662 | B2 | | 12/2014 | Sherwood |
| 9,352,061 | B2 | | 5/2016 | Crowe |
| 2004/0235410 | A1 | * | 11/2004 | Matulevich ............. A61L 9/12 454/275 |
| 2006/0111012 | A1 | * | 5/2006 | Machala ................ A63H 3/06 446/226 |
| 2009/0191787 | A1 | | 7/2009 | Rubinstein |
| 2013/0093108 | A1 | * | 4/2013 | Scolari ................. A61L 9/122 261/146 |
| 2015/0223446 | A1 | | 8/2015 | Vaaler |
| 2015/0273100 | A1 | * | 10/2015 | David ................... A61L 9/122 40/406 |
| 2015/0292728 | A1 | * | 10/2015 | Gary ..................... G09F 19/02 362/123 |
| 2016/0228784 | A1 | * | 8/2016 | Morita ................... A63H 3/06 |
| 2017/0225090 | A1 | * | 8/2017 | Dripps ................. A63H 33/08 |

FOREIGN PATENT DOCUMENTS

| | | |
|---|---|---|
| JP | 3191142 U | 6/2014 |
| KR | 200464114 | 12/2012 |

\* cited by examiner

VENT BALLOON

BACKGROUND OF THE INVENTION

1. Technical Field

The present invention relates to balloons and inflatable objects. More specifically, the present invention relates to balloons for use over air vents.

2. Background Art

Balloons are used by many people for festive events and parties such as for birthdays, graduations, anniversaries, baby showers, retirements, and holidays. Helium balloons can be filled at a store but then must be transported to the home or event site in a car and can be cumbersome. Other standard balloons can be filled by blowing air at the home, but this can also be difficult and tiresome.

A balloon has been designed to fit over an air vent to be inflated by air flowing out of the air vent. U.S. Pat. No. 5,186,675 to Stoddard discloses an inflatable vent toy for an exhaust vent air outlet including an inflatable balloon made of a flexible material patterned and shaped to suit the preference of a user having a base defining an air inlet with surrounding attachment structure to secure the base over the exhaust vent air outlet such that the air inlet is in communication with the vent air outlet to enable in-coming air from the vent to enter the base air inlet and fill the balloon in a first mode, and to escape and collapse in a second mode when the in-coming air from the vent stops. The base structure is generally removably attached to the vent with magnets, ties, hooks, or straps. The inflatable vent toy can be in shapes such as a ghost or goblin, or contain pictures of athletes or movie characters.

There are several disadvantages to using a vent balloon with a base of corrugated cardboard, such as product liability using over a hot air vent, and the cheap looking quality of the cardboard. Therefore, there remains a need for a balloon that is easy to use in the home that can effectively make use of air from an air vent that is also safe to use.

SUMMARY OF THE INVENTION

The present invention provides for a vent balloon including an inflatable body operatively attached to a molded plastic base on a proximal side, wherein the inflatable body is inflated by a mechanism of an air vent or a fan operatively attached to the molded plastic base, and including a scent mechanism operatively attached to the molded plastic base for dispersing scent in a room that relates to a design on the inflatable body.

The present invention also provides for a method of using a vent balloon by flowing air through an inflatable body of a vent balloon through a molded plastic base, wherein the air comes from a source of an air vent or a fan operatively attached to the molded plastic base, inflating the inflatable body, and flowing air over at least one scent mechanism operatively attached to the molded plastic base that relates to a design on the inflatable body and releasing scent into the air.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
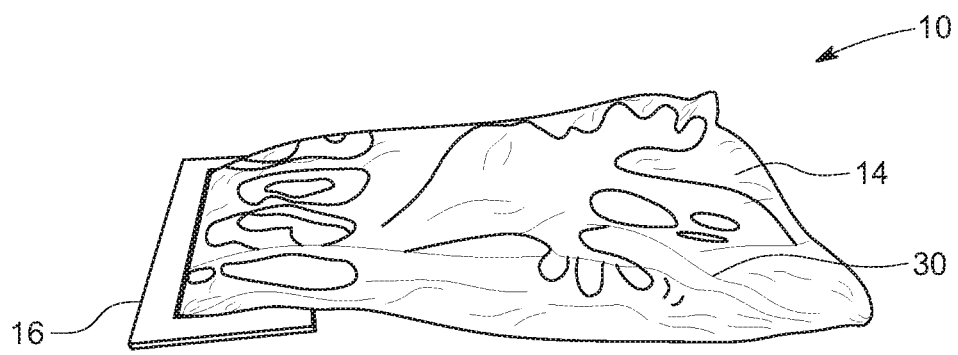
FIG. 1 is a photograph of a vent balloon of the present invention.
Figure 2:
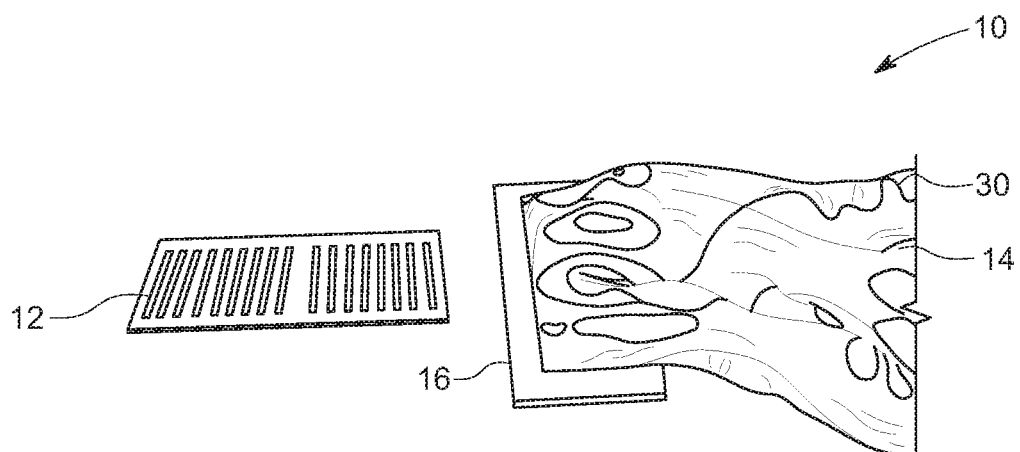
FIG. 2 is a photograph of the vent balloon beside an air vent.
Figure 3:
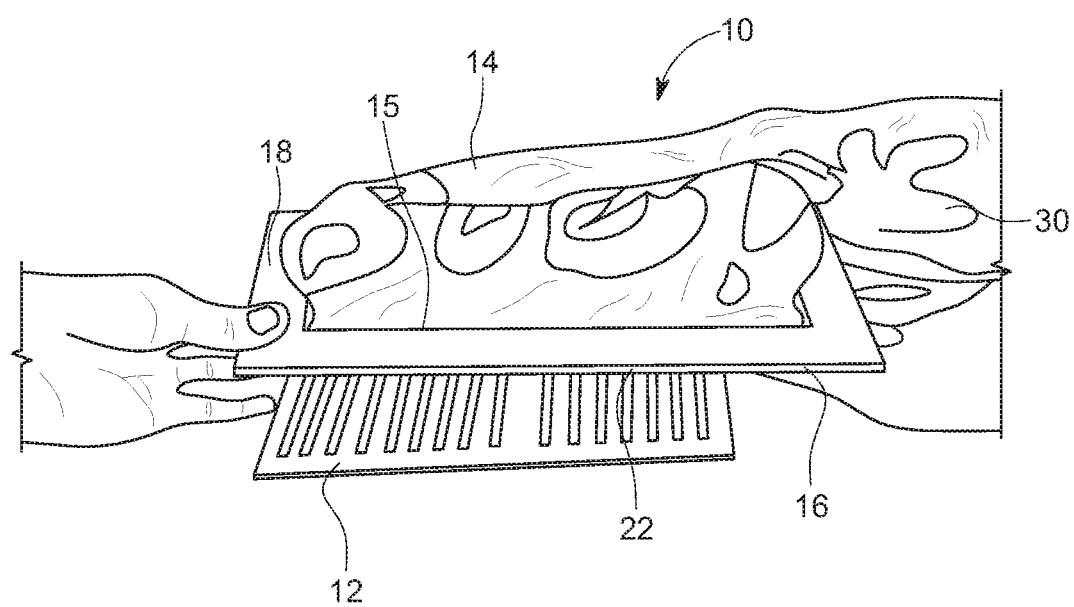
FIG. 3 is a photograph of placement of the vent balloon over the air vent.
Figure 4:
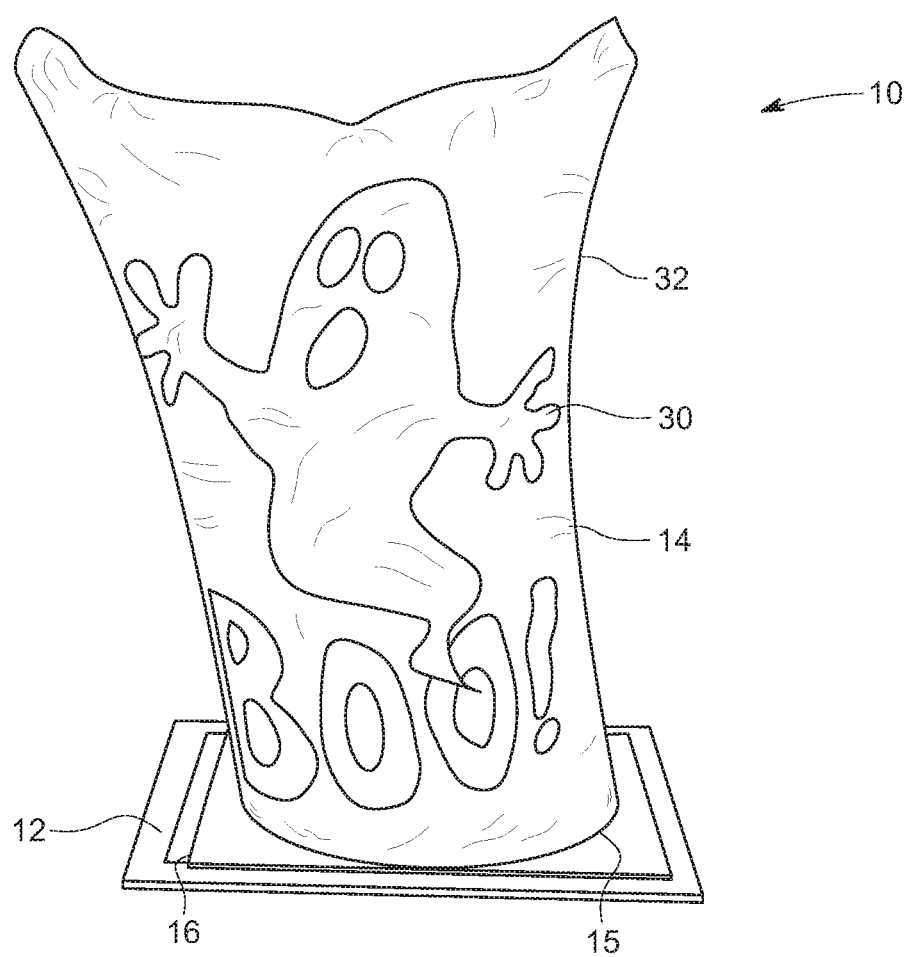
FIG. 4 is a photograph of the vent balloon inflated and positioned over the air vent.

The present invention provides for a vent balloon, shown at 10 in the FIGURES, that is inflatable by either cold or hot air flowing through an air vent 12 when placed over the air vent 12. The vent balloon 10 includes an inflatable body 14 operatively attached to a base 16 on a proximal side 18, and a removable adhesive 20 attached to a distal side 22 of the base 16.

Figure 5:
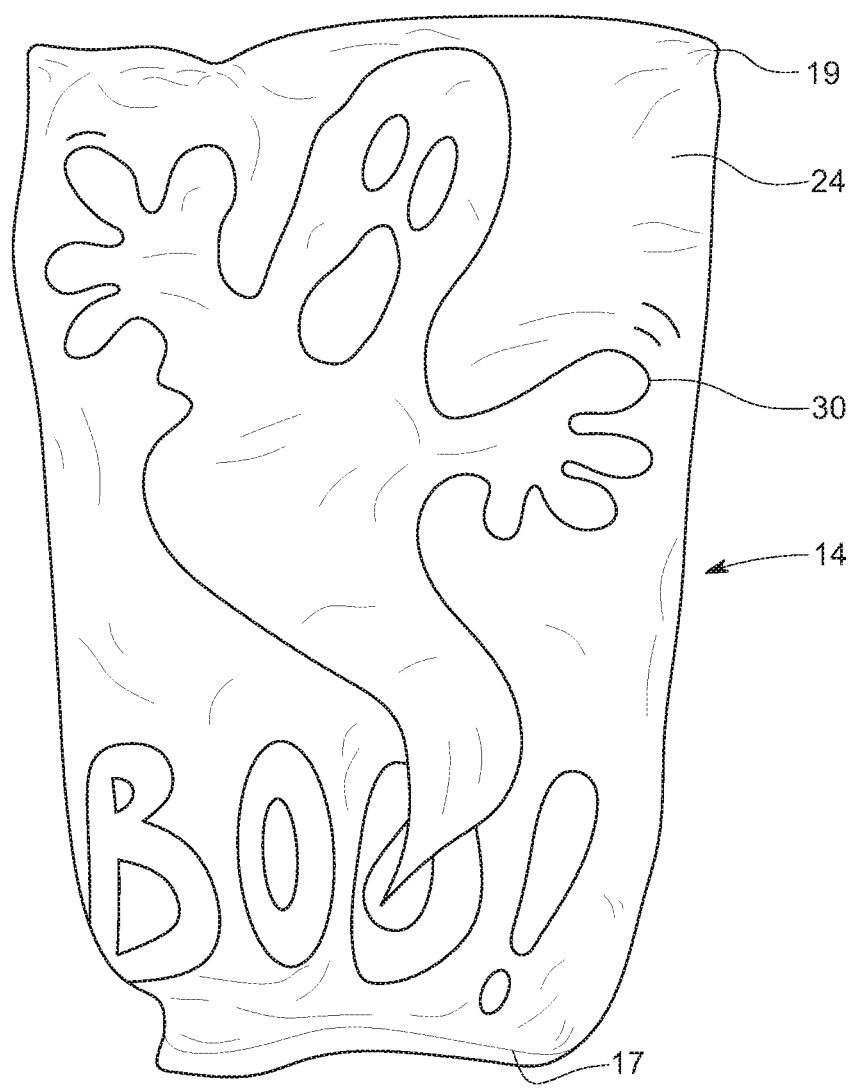
FIG. 5 is a photograph of a lay-flat polyethylene bag.
Figure 8A:
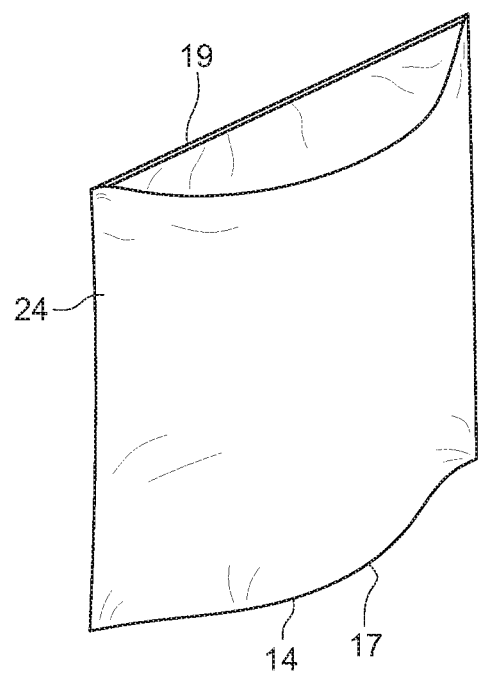
FIG. 8A is a schematic of a lay-flat polyethylene bag and FIG. 8B is a photograph of an inflated lay-flat polyethylene bag vent balloon.
Figure 8B:
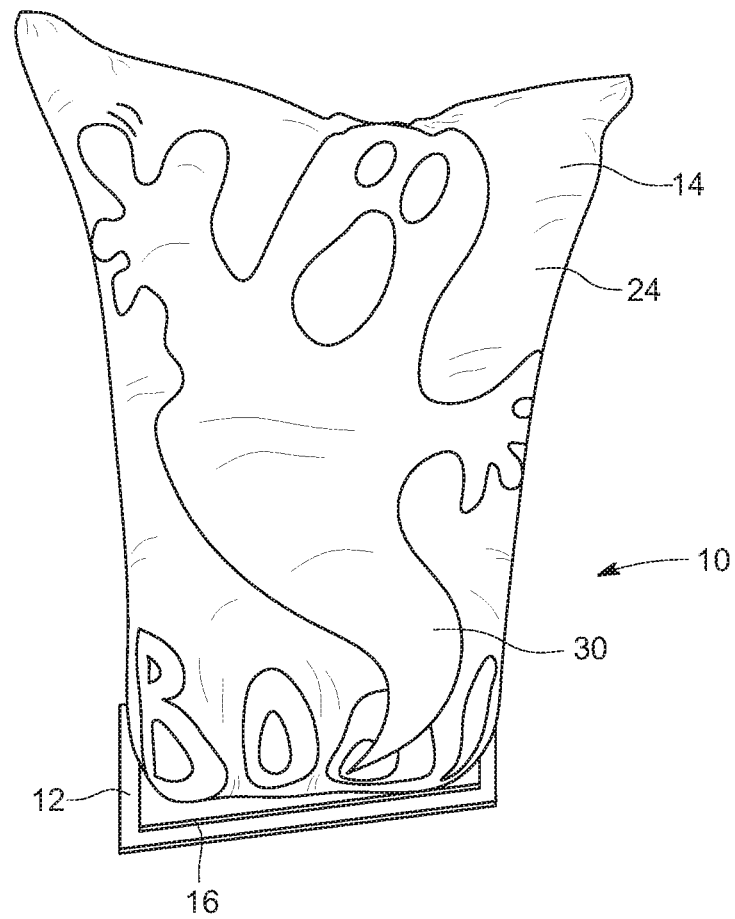
Figure 9A:
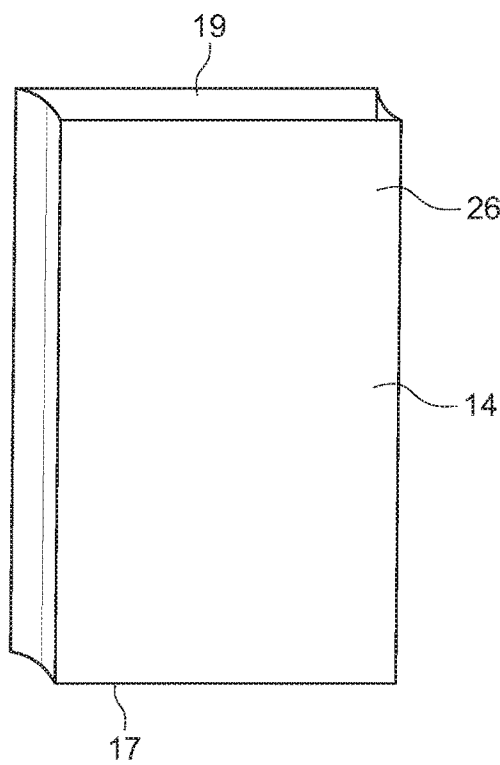
FIG. 9A is a schematic of a gusseted polyethylene bag and FIG. 9B is a side perspective view of an inflated gusseted polyethylene bag vent balloon.
Figure 9B:
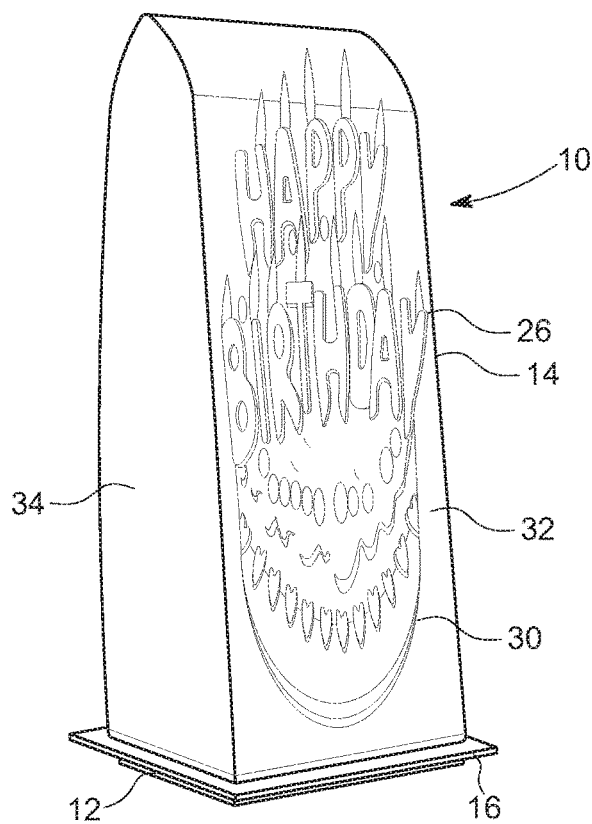
Figure 13:
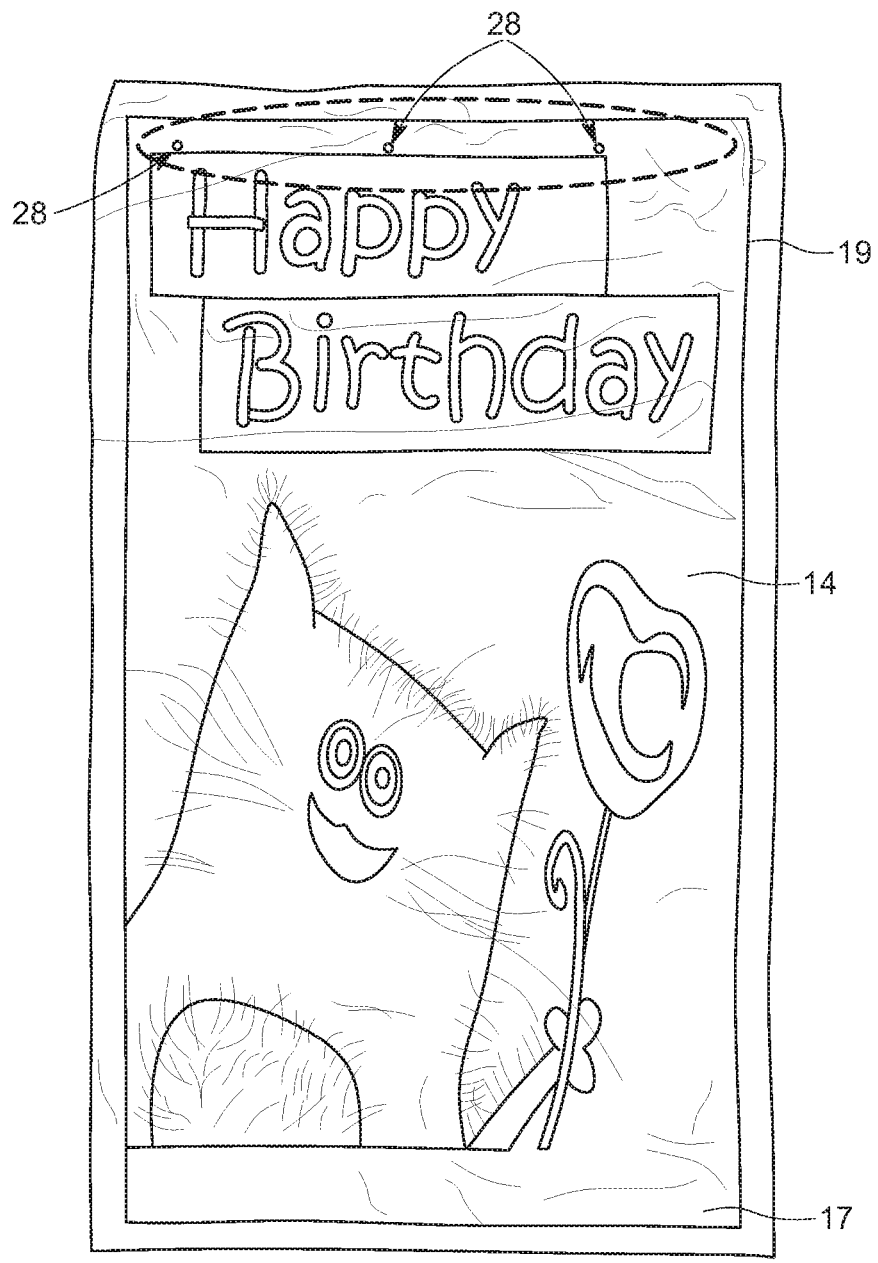
FIG. 13 is a front view of the inflatable body with vents.

The inflatable body 14 is preferably a polyethylene bag having an open end 17 and a closed end 19. The inflatable body 14 can also be made of MYLAR® (DuPont, biaxially-oriented polyethylene terephthalate), or foil. The open end 17 is operatively attached to the base 16 with an air tight seal. In one embodiment, the inflatable body 14 is a lay-flat polyethylene bag 24, shown in FIGS. 1-5, 7, and 8A-8B. The lay-flat polyethylene bag 24 is shown without the base 16 in FIGS. 5 and 8A. In another embodiment, the inflatable body 14 is a gusseted polyethylene bag 26, shown in FIG. 9A without the base 16 and in FIG. 9B with the base 16. The inflatable body 14 can include at least one vent 28 that can essentially be a slit in the inflatable body 14 at any suitable location in order to let air gradually release from and flow through the vent balloon 10 while still allowing the inflatable body 14 to stand upright, shown in FIG. 13. Various sizes of the vent balloon 10 can have different numbers of vents 28. For example, a 20" tall inflatable body 14 can have three vents 28 or four vents 28, each ¼" diameter in size, in a row near the closed end 19 of the inflatable body 14. A 26" tall inflatable body 14 can have three vents 28 or four vents 28, each ½" diameter in size. A 30" tall inflatable body 14 can have three vents 28 or four vents 28, in any suitable diameter size.

The inflatable body 14 further includes a design 30 imprinted on a front side 32 or on both the front side 32 and a back side 34. The design 30 can be the same on the front side 32 and back side 34, or different on each side 32, 34. The design 30 can be a holiday greeting, congratulations, a personal message, cartoon characters, general celebratory designs, or promotional advertisements. The inflatable body 14 can also be any desired color (including metallic) and the design 30 can be any desired color. The inflatable body 14 can further be a rectangular shape or a die cut shape.

Figure 11A:
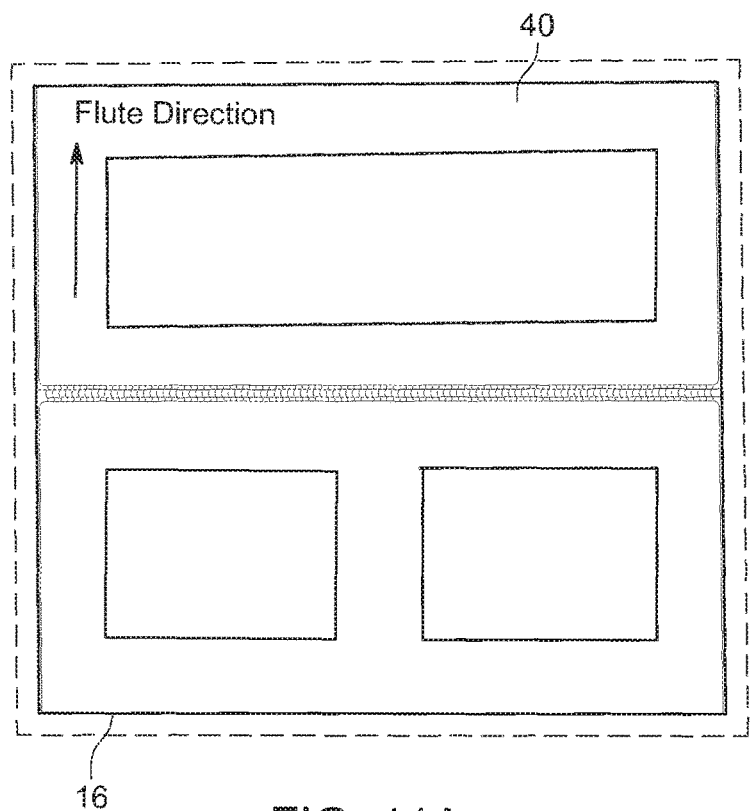
FIGS. 11A and 11B are top views of a base with different flute directions.
Figure 11B:
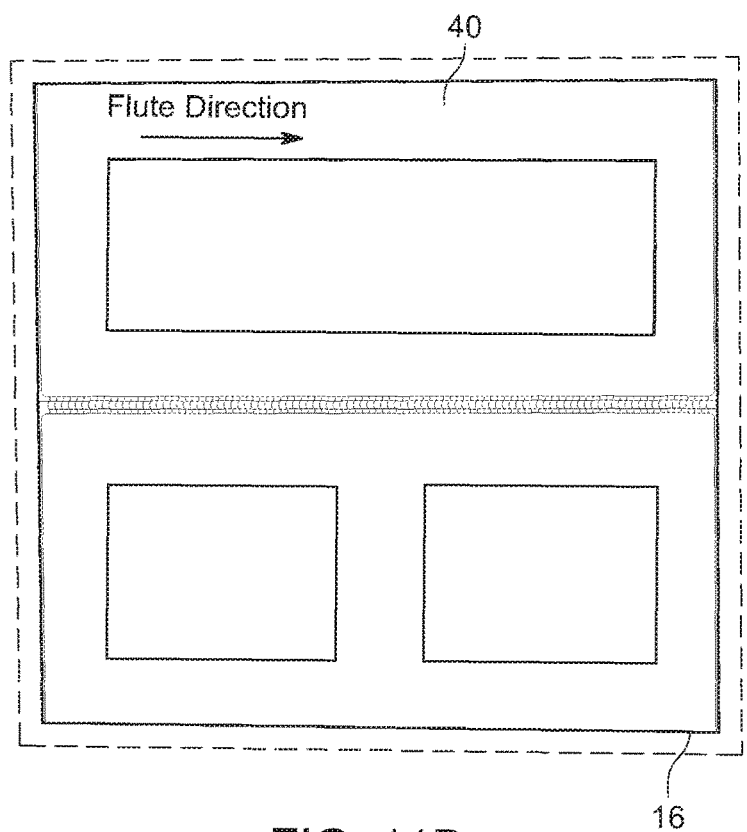
Figure 23:
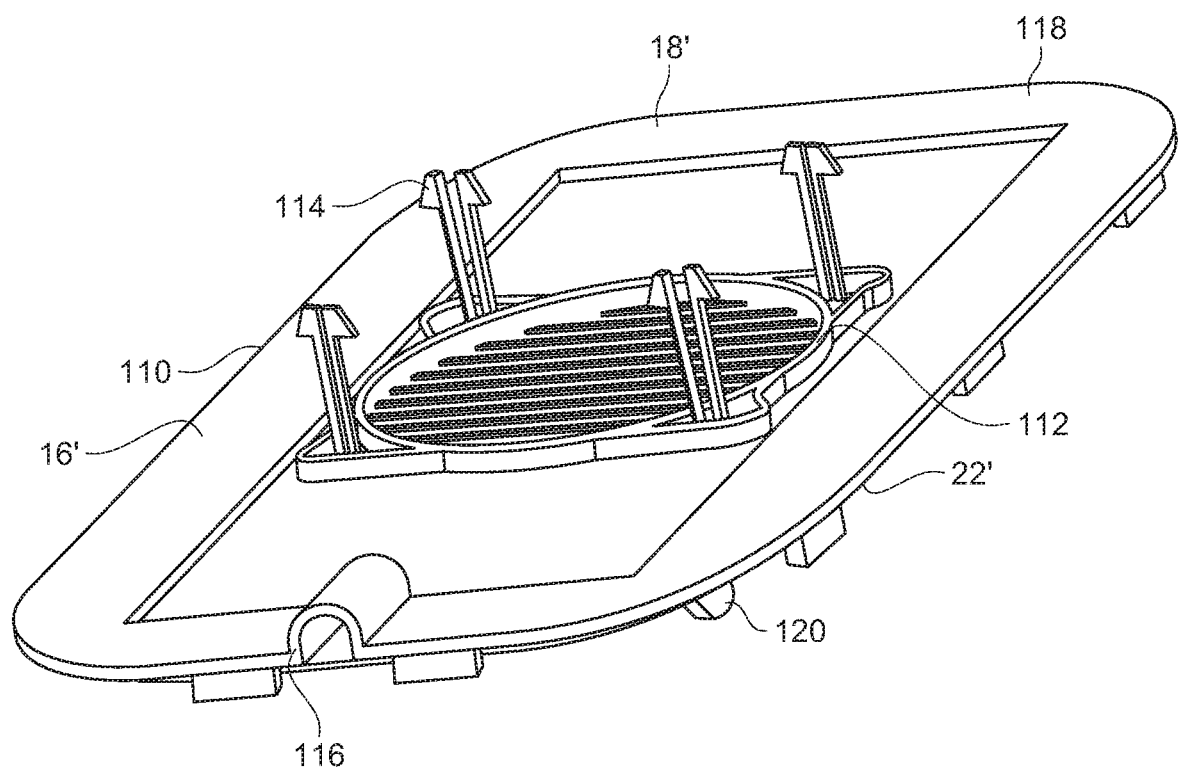
FIG. 23 is a top perspective view of a molded plastic base.

The inflatable body 14 is operatively attached to the base 16 entirely at a bottom end 15 by an adhesive glue or any other suitable mechanism. The base 16 is shown in FIGS. 1-5, 6-7, 8B, and 9B. The base 16 is preferably made of corrugated cardboard, corrugated plastic (fluted polypropylene plastic), or molded plastic 110 that is die cut (as shown in FIG. 23). Preferably, the base 16 is made from 2.5 mm thick fluted polypropylene plastic. The base 16 can have flutes 40 that preferably run in a vertical direction, shown in FIG. 11A. This allows for the mailing of the vent balloon 10 to be in a flexible package, reducing mailing costs. Less preferably, the base 16 can have flutes 40 running in a horizontal direction, shown in FIG. 11B, however, this would increase mailing costs. The base 16 can be any suitable shape and size to fit over and adhere to standard air vents 12, and preferably in a rectangular shape. The vent balloon 10 can also preferably be sized to fit inside an 11.5" by 5.25" envelope for mailing through regular mail processing. The base 16 is preferably substantially a flat and/or planar body.

Figure 6A:
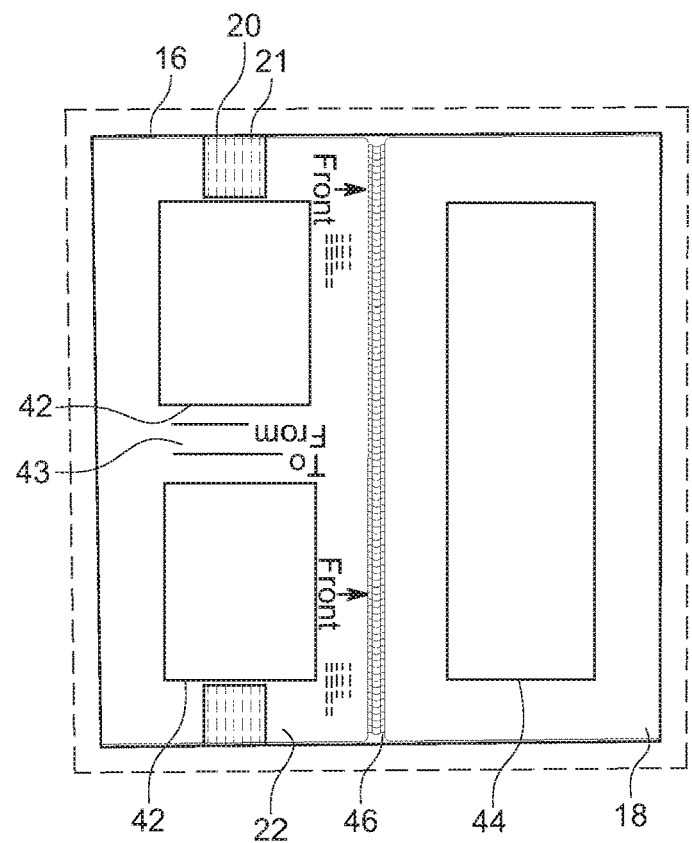
FIGS. 6A-6G are views of the assembly of the base with the inflatable body.
Figure 6B:
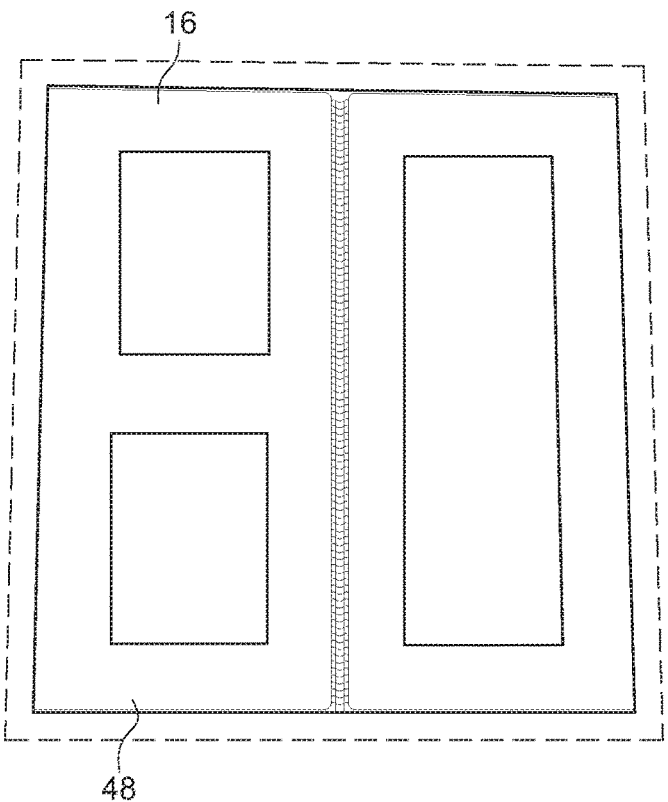
Figure 6C:
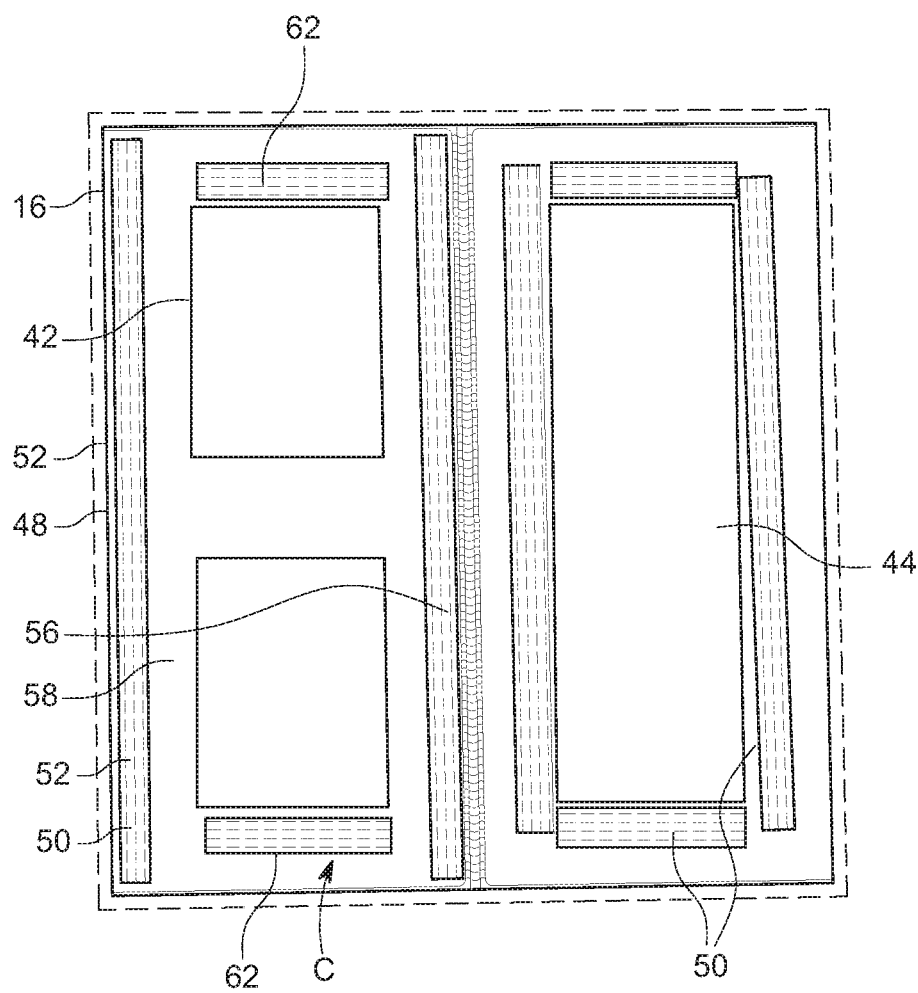
Figure 24:
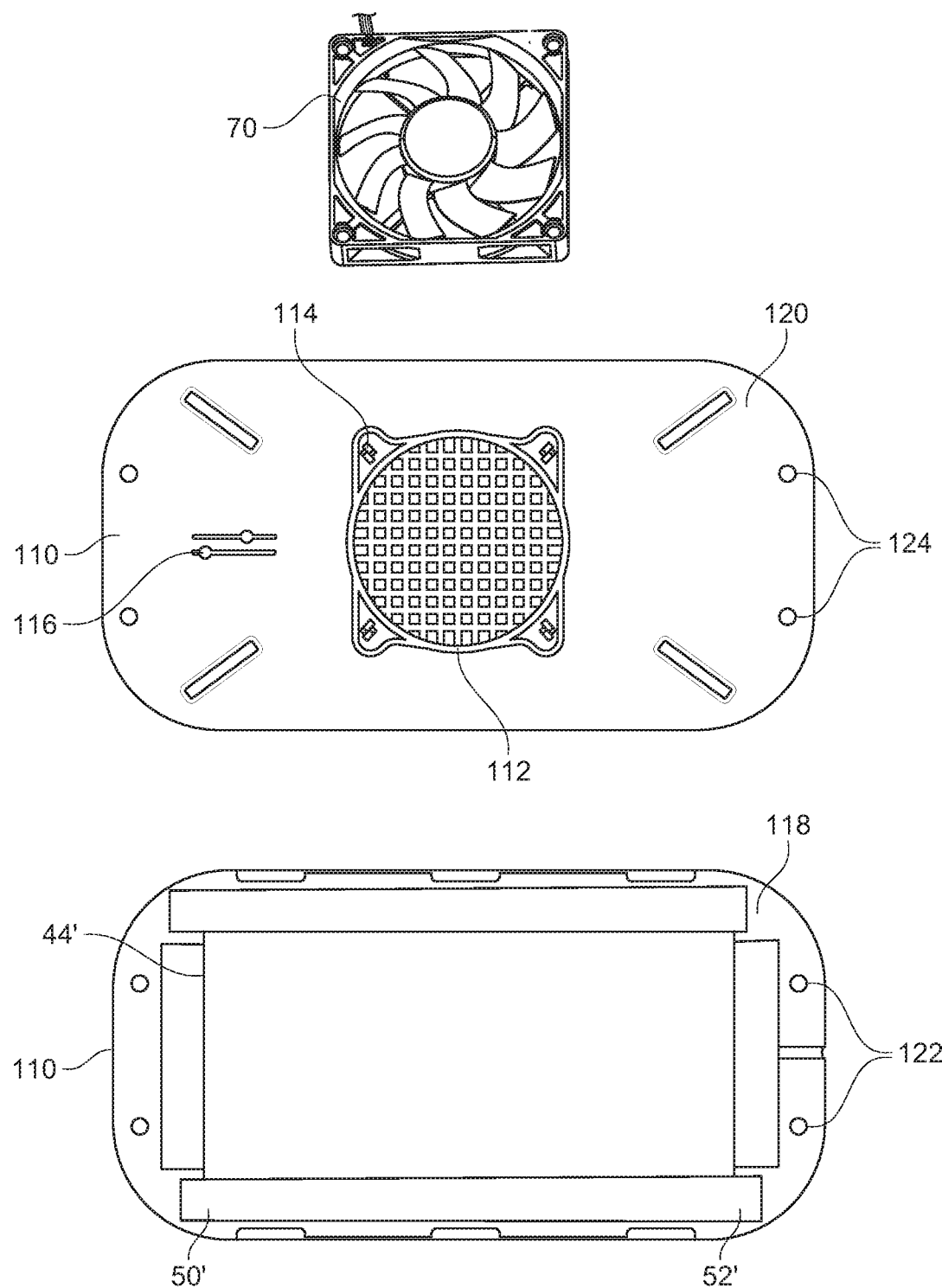
FIG. 24 is an exploded view of a molded plastic base and fan.

The base 16 can be manufactured as shown in FIGS. 6A-6G and then folded into a rectangular shape. FIG. 6A shows the distal side 22 of the base 16 and the proximal side 18, joined at a center seam 46. The distal side 22 can include at least one distal facing cutout 42 (two are shown in the FIGURES separated by a central bar 43), and the proximal side 18 can include a proximal facing cutout 44. FIG. 6B shows an inner side 48 of the base 16 before an inner adhesive 50 has been applied. FIG. 6C shows the inner side 48 after inner adhesive 50 has been applied, which can be an adhesive tape with a protective liner 52 or hot melt glue. The inner adhesive 50 secures the inflatable body 14 to the base 16. Inner adhesive 50' with protective liner 52' is also shown in FIG. 24 with a molded plastic base 110. The inner adhesive 50 can be located in any suitable position to secure the inflatable body 14, but preferably surrounding the proximal facing cutout 44 (or 44') and an inner edge 54 and outer edge 56 of the inner distal side 58 as shown in FIG. 6C. Additional filter or scent mechanism adhesives 60 can also be included on the inner distal side 58.

Figure 6D:
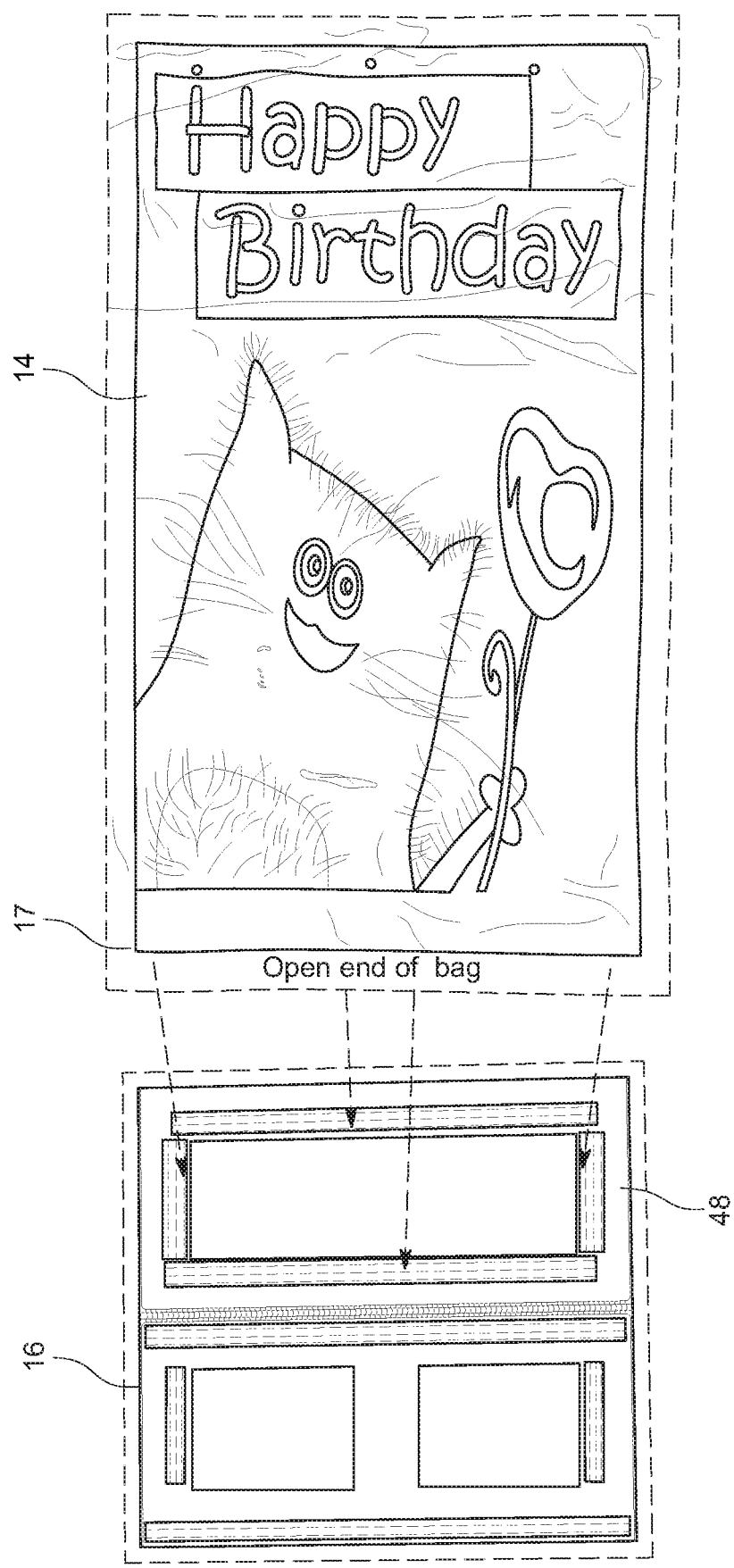
Figure 6E:
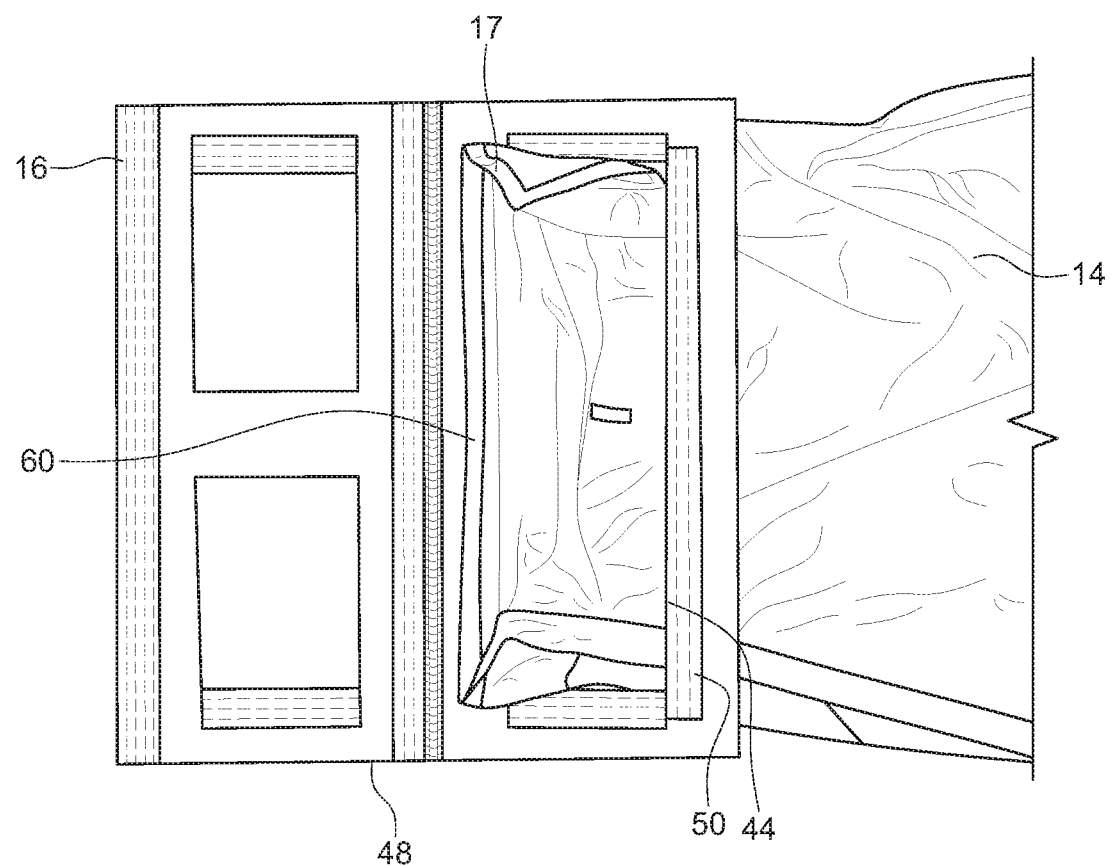
Figure 6F:
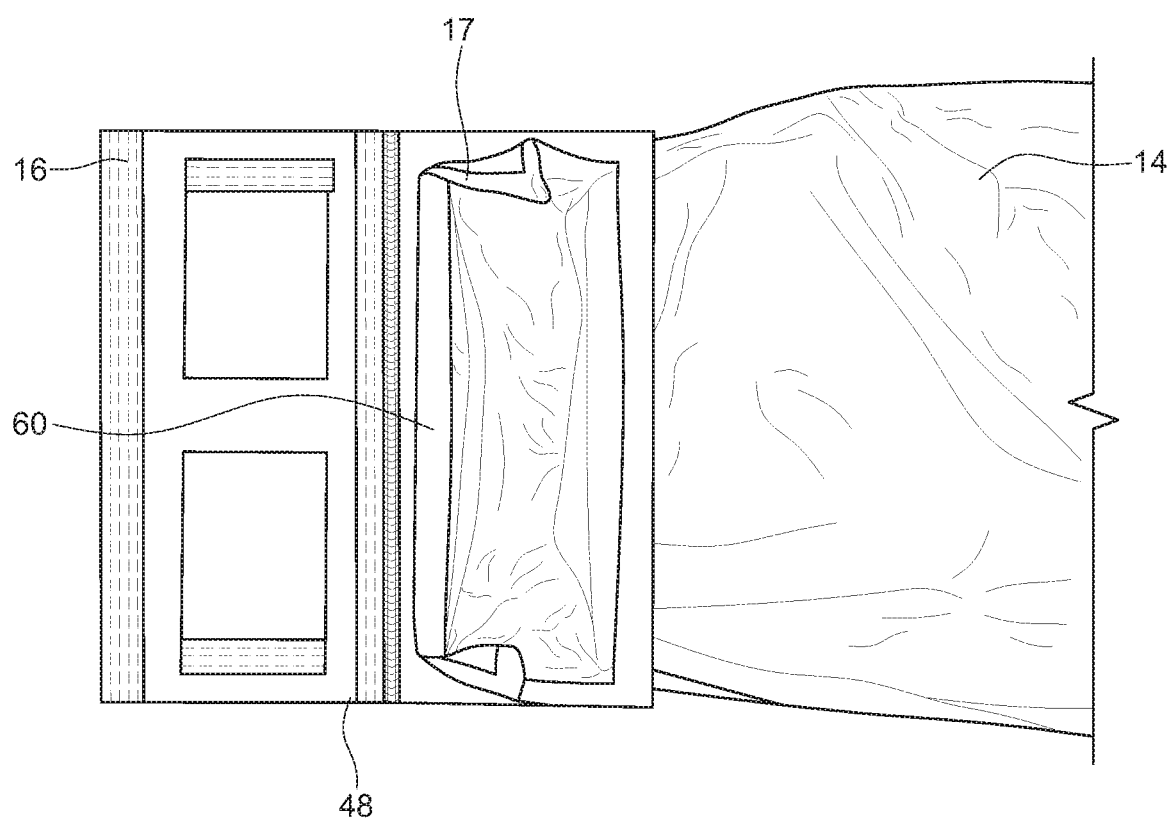
Figure 6G:
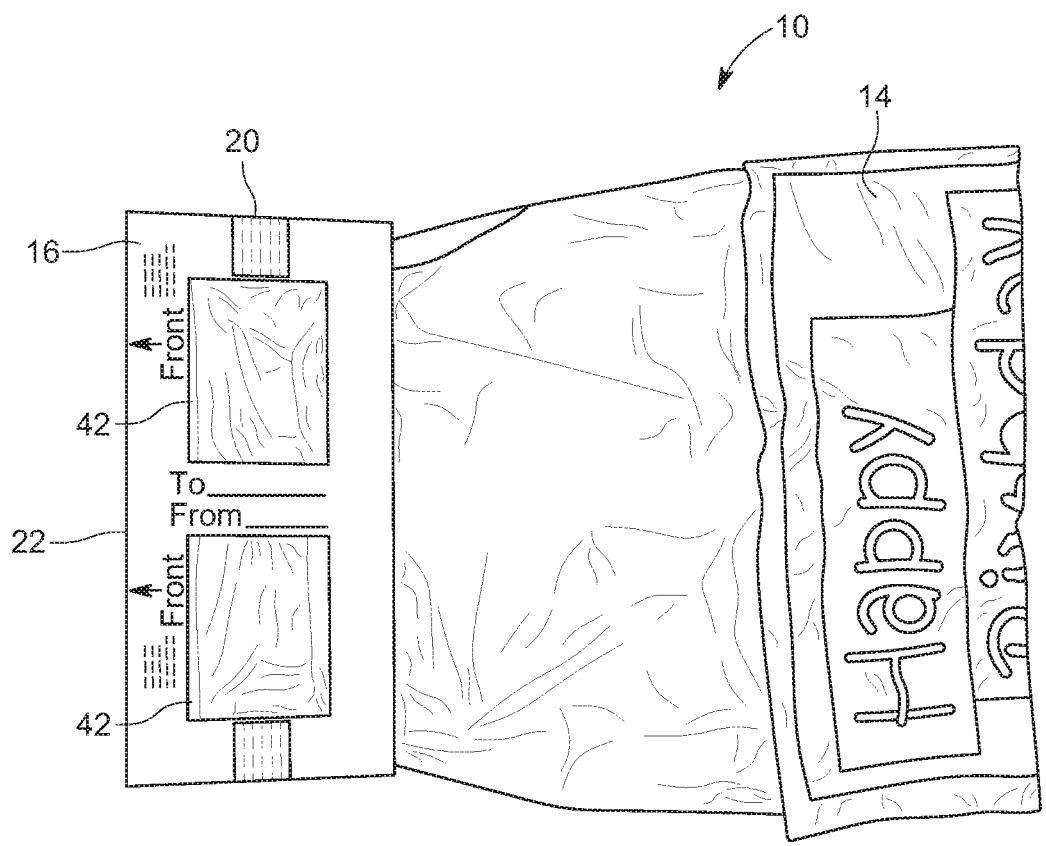
Figure 7:
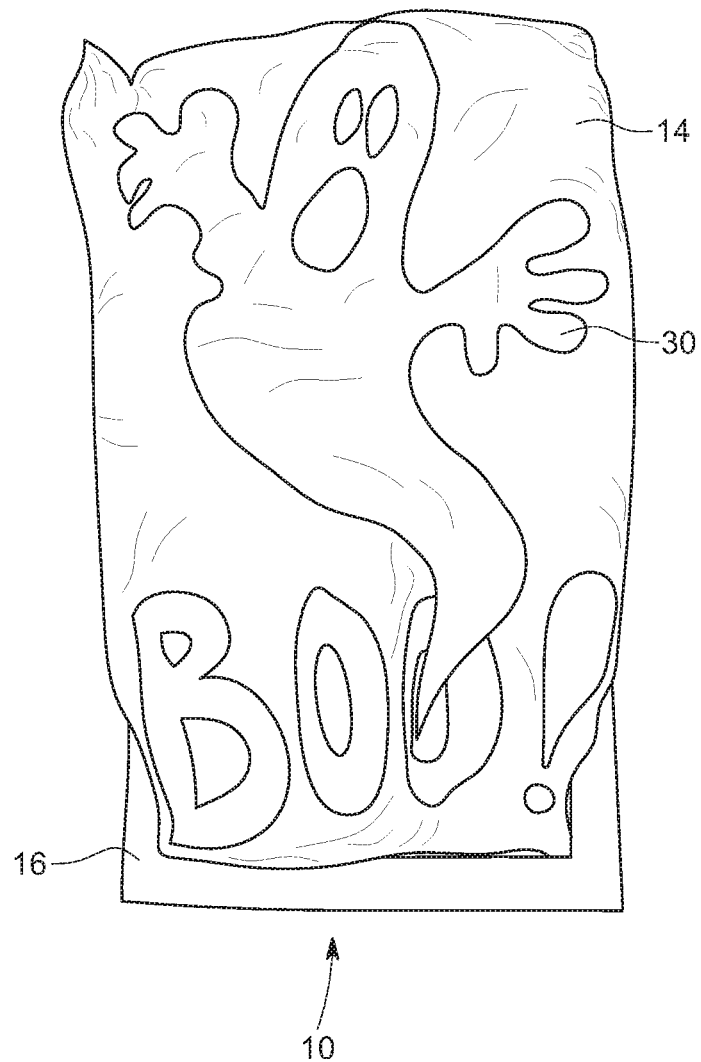
FIG. 7 is a photograph of an assembled vent balloon.

FIG. 6D shows the inflatable body 14 positioned to be attached to the base 16 at the open end 17. Any protective liners 52 on the inner adhesive 50 along the proximal facing cutout 44 are removed to expose the adhesive. The open end 17 of the inflatable body 14 is pulled through the proximal facing cutout 44 from the proximal side 18 to the inner side 48 and an edge 60 of the open end 17 is secured by the inner adhesive 50 (FIG. 6E (partly attached) and 6F (completely attached)). In the final step, any protective liners 52 on the inner adhesive 50 along the inner edge 54 and outer edge 56 of the inner distal side 58 are removed. The distal side 22 is folded to meet the proximal side 18 along the center seam 46, as shown in FIG. 6G, resulting in the assembled vent balloon 10.

The removable adhesive 20 on the distal side 22 of the base 16 can be covered by removable protective strips 21 that protect the removable adhesive 20 until the vent balloon 10 is used. The removable adhesive 20 remains attached to the distal side 22 but allows the distal side 22 to be easily removed from the air vent 12, and can be used on any type of air vent 12, including wood, plastic, and painted air vents 12. The removable adhesive 20 can also be reusable once the vent balloon 10 has been removed. The removable adhesive 20 can optionally be magnetic tape that can secure to steel vents with magnetic force.

The present invention also provides for a method of using the vent balloon 10, by removably adhering the inflatable body 14 through the base 16 to an air vent 12, flowing air through the inflatable body 14, and inflating the inflatable body 14. More specifically, the distal side 22 of the base 16 is removably adhered to the air vent 12. Once the vent balloon 10 is inflated, the inflatable body 14 stands upright and the design 30 is displayed and visible. A portion of the air also flows through vents 28 out of the inflatable body 14 such that the vent balloon 10 maintains its inflated shape without lifting off of the air vent 12. The vent balloon 10 can include any of the features described above, and can use a lay-flat polyethylene bag or gusseted polyethylene bag, and include any design. The vent balloon 10 can also be initially folded, obscuring or hiding the design, and once placed over the air vent 12, the inflatable body 14 unfolds and inflates to reveal the design 30, especially to reveal a surprise message.

Figure 10:
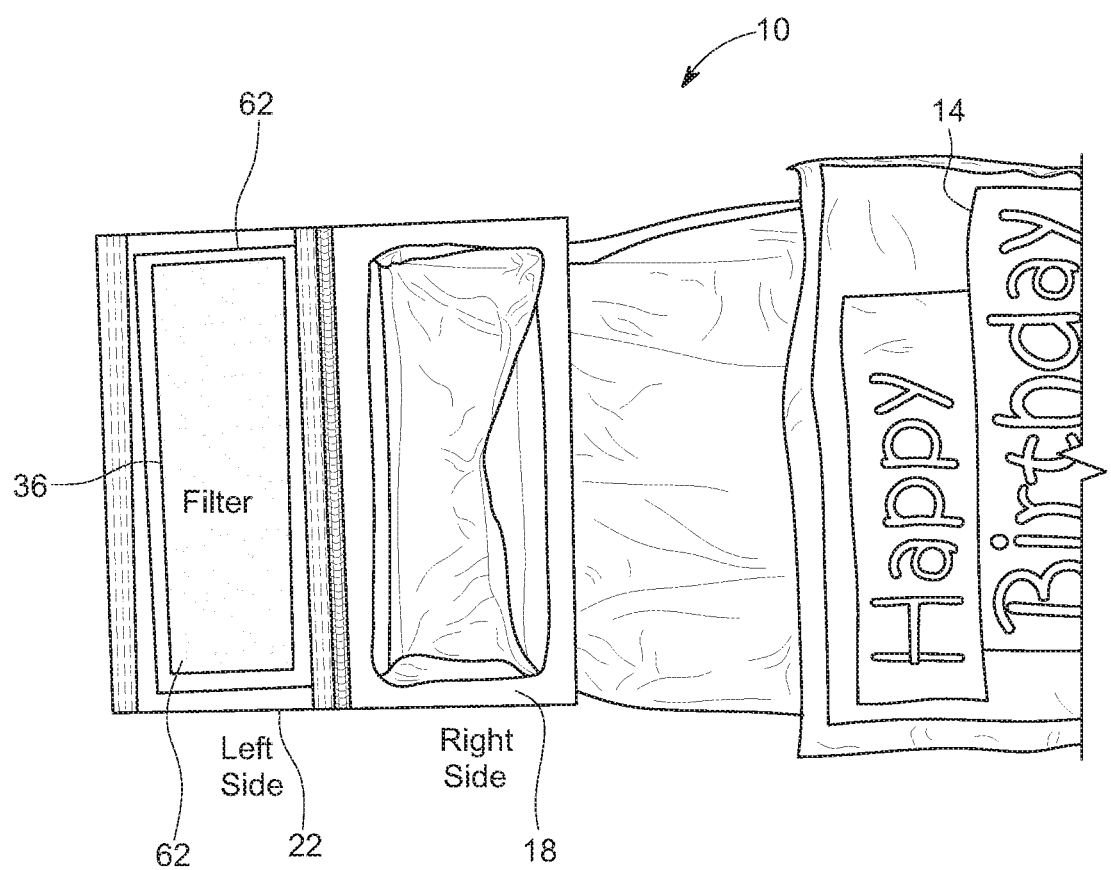
FIG. 10 is a view of a filter/scent mechanism with the base.
Figure 12:
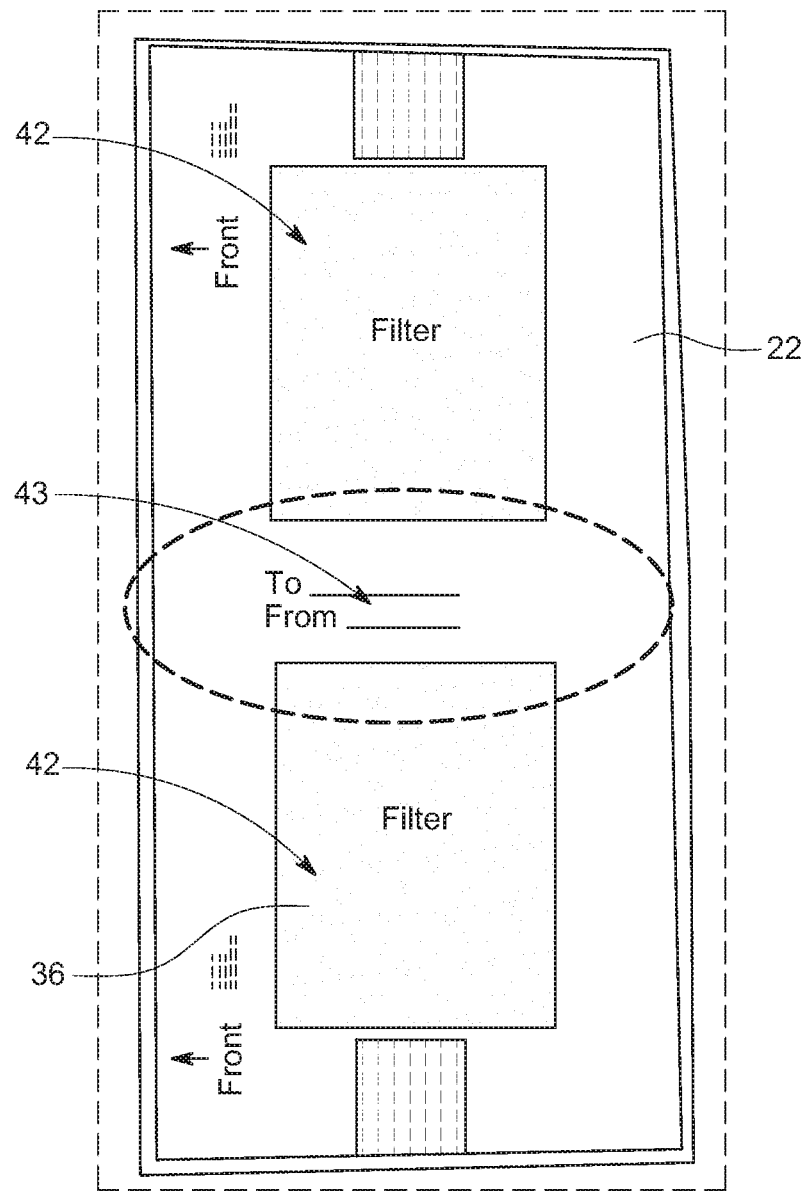
FIG. 12 is a bottom view of a filter/scent mechanism in the base.

The vent balloon 10 can also further include at least one filter or scent mechanism 36, shown in FIG. 10, that is activated upon air flowing through the vent balloon 10 from the air vent 12 and out through the vents 28 to disperse scent in a room. The filter/scent mechanism 36 can be operatively attached with a filter adhesive 62 in any suitable location, such as on the inner side 48 of the base 16 (shown in FIG. 10) or on an inside 38 of the inflatable body 14. After attaching the inflatable body 14 as in FIG. 6F, the filter/scent mechanism 36 can be attached to the filter adhesive 62 (after removing any protective liner 52), and then the distal side 22 folded to meet the proximal side 18 as in FIG. 6G. The central bar 43 provides support to the filter/scent mechanism 36, as shown in FIG. 12. The filter 36 can be unscented, or the scent mechanism 36 can include a scent related to the design 30, such as a pumpkin spice scent for a Halloween or fall design, a peppermint scent for a Christmas design, a rose or peppermint scent for Valentine's Day or anniversary design, a rose scent for Mother's Day, or a cake scent for a birthday design. The scent mechanism 36 can include a container holding a gel or oil containing scent therein that releases the scent when air flows past.

A musical chip can also be included on the center bar 43 for music associated with the design 30.

Therefore, the present invention provides for a vent balloon 10 for dispersing scent in a room, including an inflatable body 14 operatively attached to a base 16 on a proximal side 18, a removable adhesive 20 attached to a distal side 22 of the base 16 for attaching to an air vent 12, and at least one scent mechanism 36 operatively attached to the vent balloon 10 for dispersing scent in the room.

The present invention also provides for a method of dispersing scent in a room, by removably adhering the inflatable body 14 of the vent balloon 10 through the base 16 to an air vent 12, flowing air through the inflatable body 14 and over at least one scent mechanism 36, releasing scent into the air, inflating the inflatable body 14, and flowing scented air through vents 28 on the inflatable body 14 into the room. As above, more specifically, the distal side 22 of the base 16 is removably adhered to the air vent 12. Once the vent balloon 10 is inflated, the design 30 is visible. A portion of the air also flows through vents 28 out of the inflatable body 14 such that the vent balloon 10 maintains its inflated shape without lifting off of the air vent 12. The vent balloon 10 can include any of the features described above, and can use a lay-flat polyethylene bag or gusseted polyethylene bag, and include any design.

Figure 14:
FIG. 14 is a front view of a table top vent balloon powered by a laptop.

In another embodiment, the vent balloon 10' can be used on any flat surface such as a table top with a fan 70 operatively attached to the base 16', wherein the fan 70 is powered through a power cord 72 for flowing air into the inflatable body 14'. The power cord 72 can be a USB power cord (including type A, type B, type C (compatible with Nexus 5X/6P, Nokia N1 tablet, One plus 3/2 LG G5), mini USB (compatible with MP3/4 players, GoPro, digital cameras), and micro USB (compatible with Android phones, BLUETOOTH® headphones, power banks), a lightning power cord (8 pins compatible with iPhone X/8/7/7plus/6s/6s plus/SE/5s/4c/5, iPad Pro Air mini), an AC/DC power cord, a cord that connects to a battery (such as a 9V battery) or battery pack, or any other suitable types of power cords. The power cord 72 can therefore, depending on type, be plugged in to a power source 74 such as desktop computers, laptops (shown in FIG. 14), tablets, smart phones, or wall outlets. The power cord 72 can be located internally in the base 16' in the case of power through a battery 100 or a battery pack 102 (either of which can be AA, AAA, or coin cells), shown in FIGS. 22A-22D. The battery 100 or battery pack 102 can be hot melted to any suitable location in the base 16'. The battery 100 or battery pack 102 can optionally include an on/off switch 104 accessible through the base 16', so that the power cord 72 does not need to be plugged in, but the on/off switch is actuated to power the vent balloon 10'.

Figure 15A:
FIG. 15A is a front view of a vent balloon with a power cord.
Figure 15B:
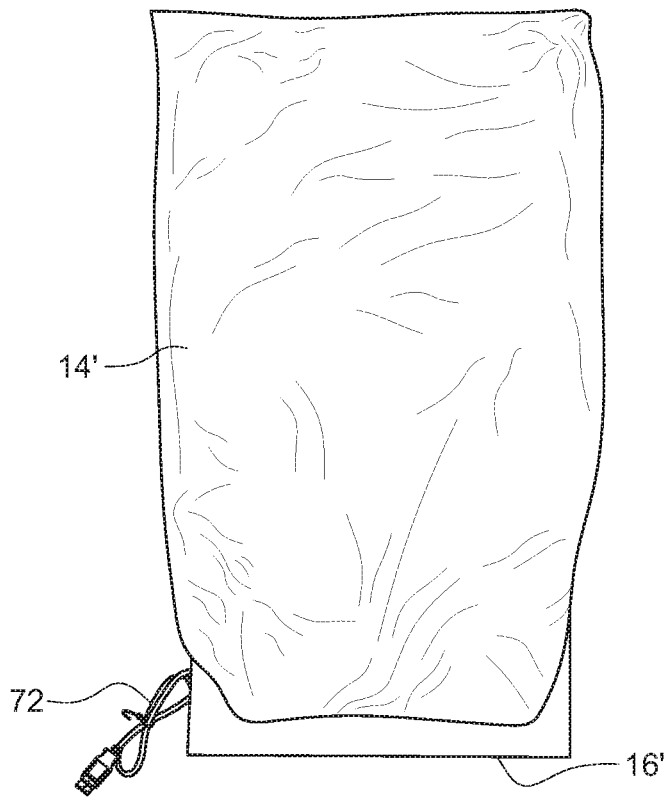
FIG. 15B is a back view of a vent balloon with a power cord.
Figure 15C:
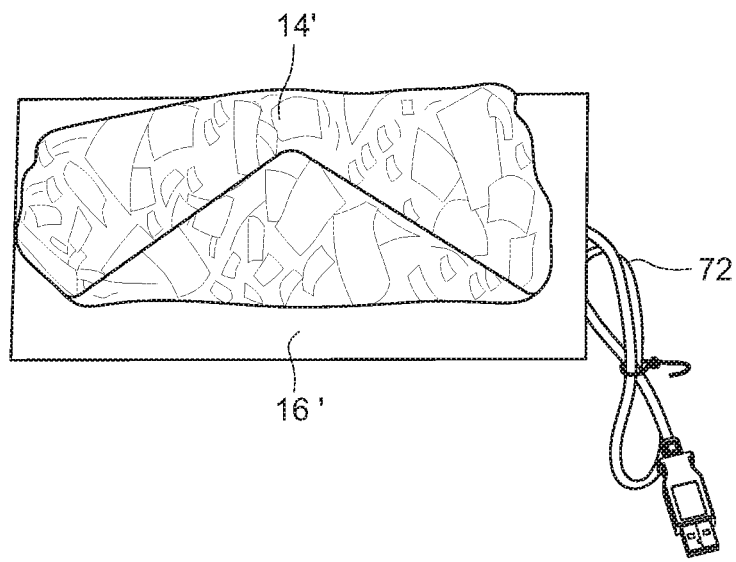
FIG. 15C is a top view of a folded inflatable body of the vent balloon with a power cord.

The vent balloon 10' includes an inflatable body 14' that can have any of the properties described above, operably attached to the base 16' as described above. FIGS. 15A, 15B, and 15C show front views, back views, and folded up views, respectively, of the vent balloon 10'. The base 16' can further have any of the properties described above.

Figure 16A:
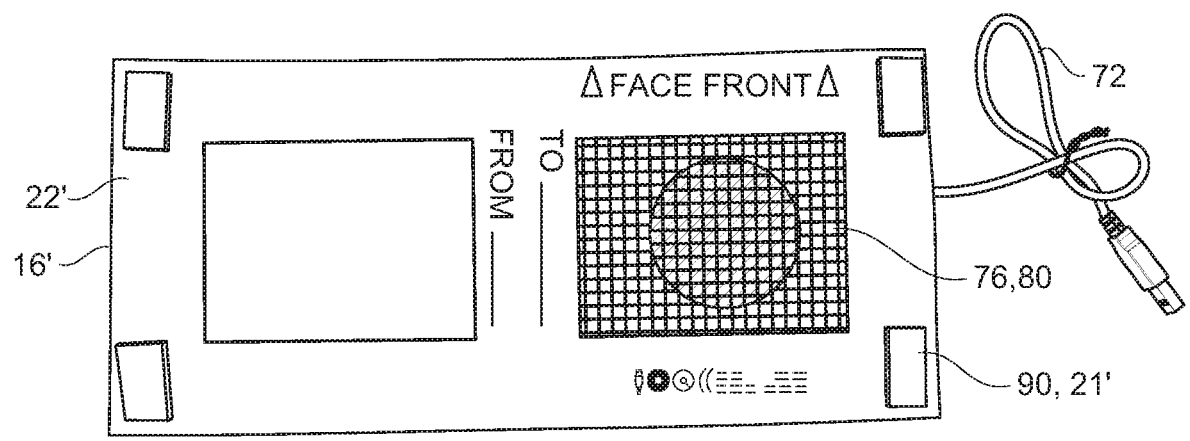
FIG. 16A is a bottom view of a base with a square vent hole.
Figure 16B:
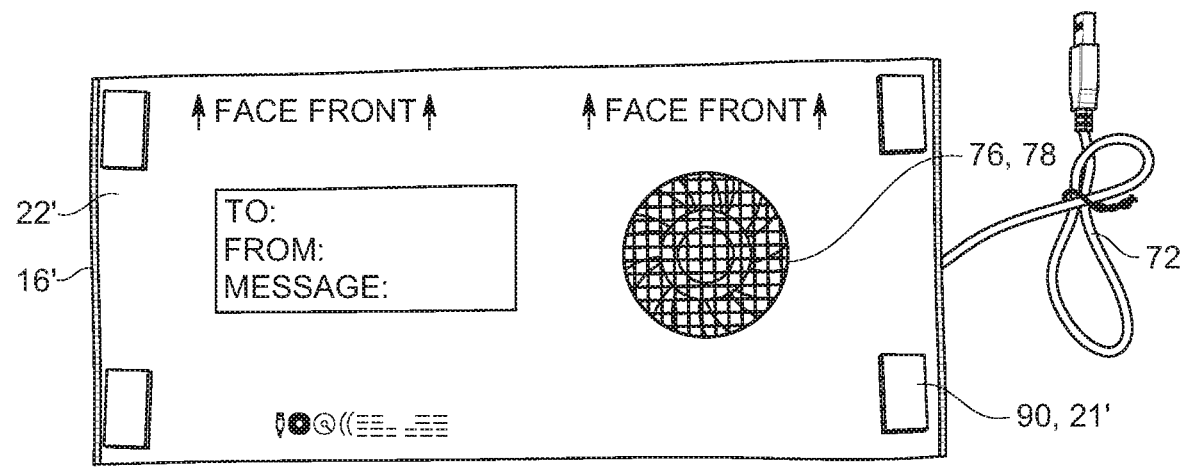
FIG. 16B is a bottom view of a base with a circular vent hole.
Figure 16C:
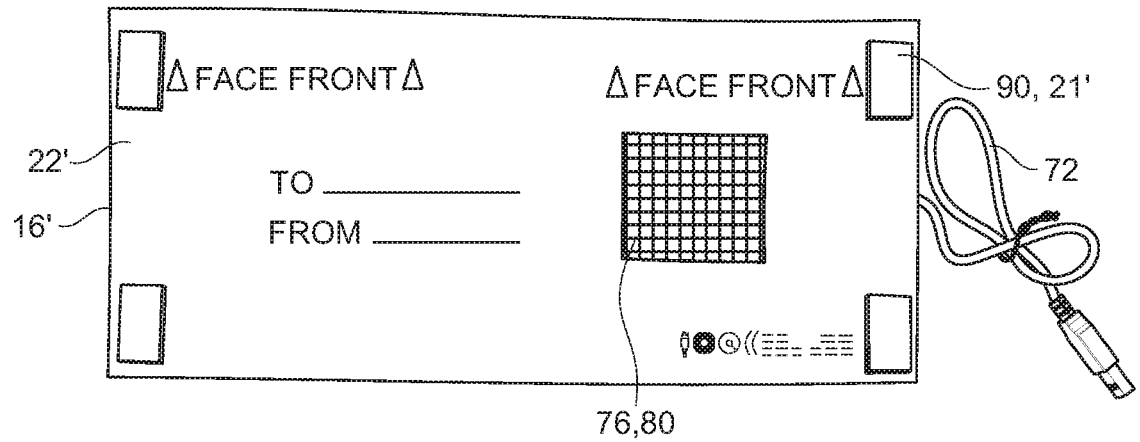
FIG. 16C is a bottom view of a base with a square vent hole.

The fan 70 can be configured in several different ways to provide a different appearance in the base 16' (shown in FIGS. 16A-16C). The base 16' or base insert 84 includes a vent hole 76 on the distal side 22' of the base 16' in either a circle shape 78 or a square shape 80 to allow for venting of the fan 70. The vent hole 76 diameter can be larger or smaller depending on the size fan 70 used, but preferably is smaller than a diameter of the fan 70. The size of the fan 70 can also be based on the size of the inflatable bag 14', and can have an air flow rating of 1800 cubic feet per minute to over 6000 cubic feet per minute.

As shown in FIGS. 17A-17F, the fan 70 can be operably attached and adhered to a proximal side 82 of a base insert 84 (preferably made of plastic) with a hot melt adhesive (or any other suitable adhesion mechanism). Next, on the distal side 86 of the base insert 84, a mesh screen 88 (preferably made of plastic or metal wire) is operably attached and adhered over the vent hole 76 with hot melt adhesive (or any other suitable adhesion mechanism). The mesh screen 88 is sized to completely cover the vent hole 76. The size of the openings of the mesh screen 88 is critical to air flow and is sized to the particular fan 70 used to achieve proper air flow to inflate a particular sized inflatable body 14'. If the openings in the mesh screen 88 are too small, air flow through the fan 70 is restricted. The openings must also be small enough not to allow an individual's finger to go through and be injured by the fan 70 if turned on. While the mesh screen 88 can be made of metal wire, this can also have a weight impact of the vent balloon 10' being sent through the mail to an individual and plastic can be preferred in models that are mailed.

Figure 17A:
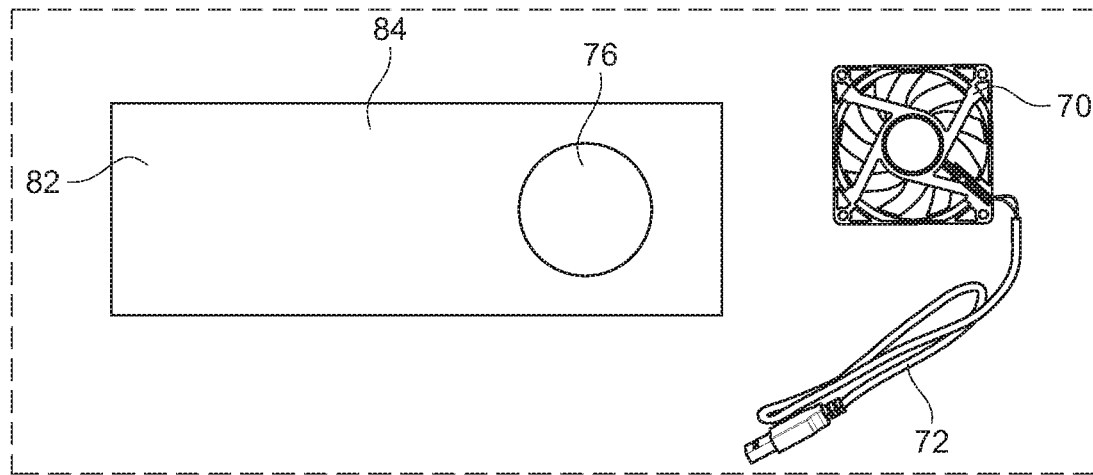
FIG. 17A is a view of a base insert and fan.
Figure 17B:
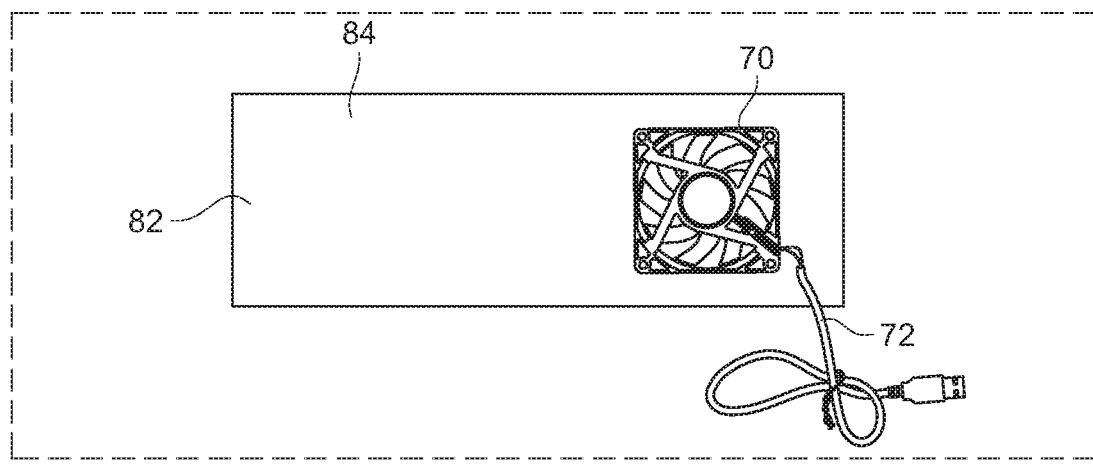
FIG. 17B is a view of a proximal side of the base insert with fan attached.
Figure 17C:
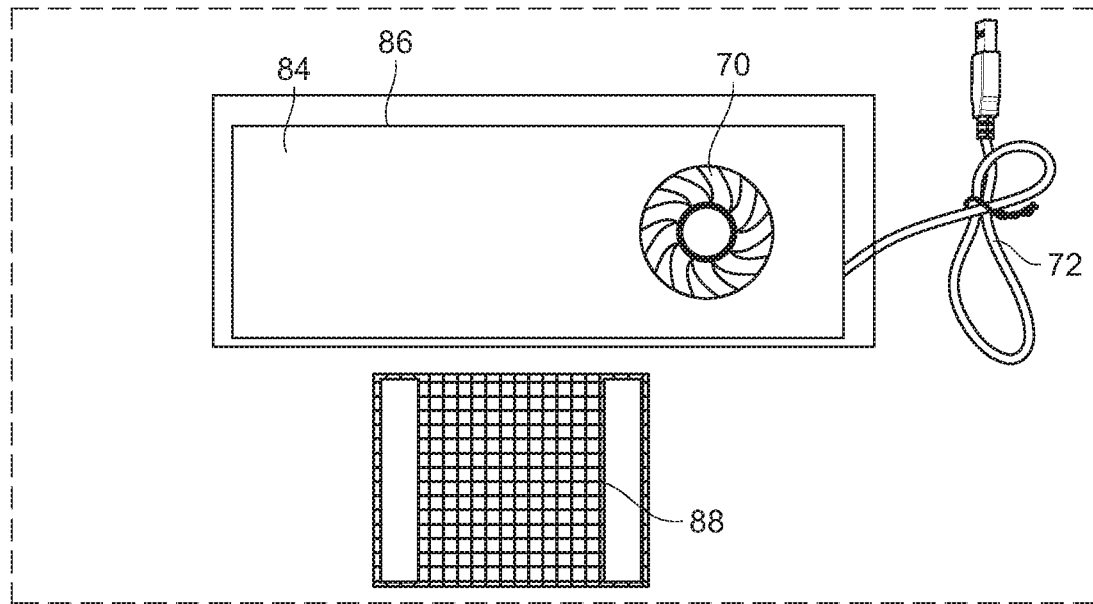
FIG. 17C is a view of a distal side of the base insert and mesh screen.
Figure 17D:
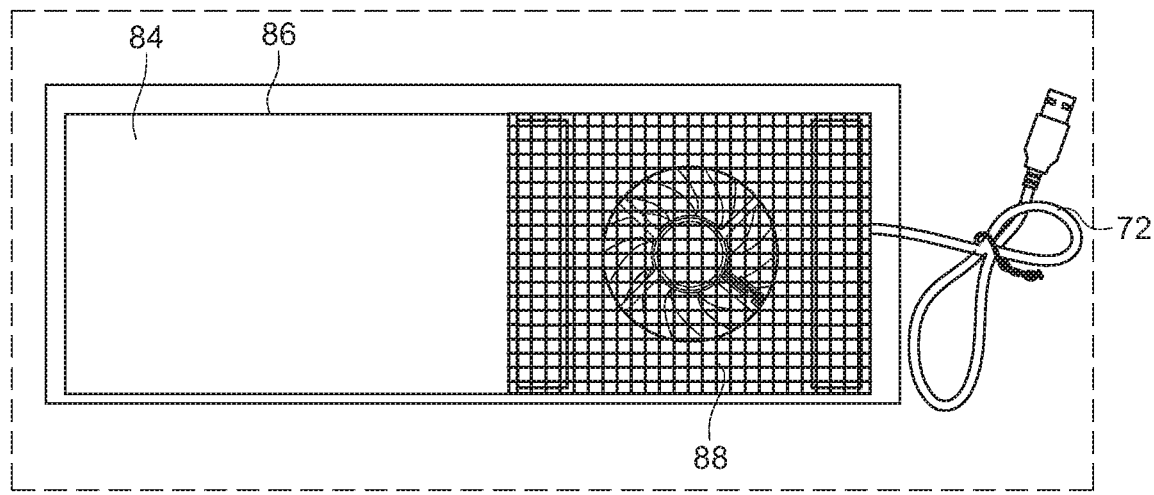
FIG. 17D is a view of a distal side of the base insert with the mesh screen attached.
Figure 17E:
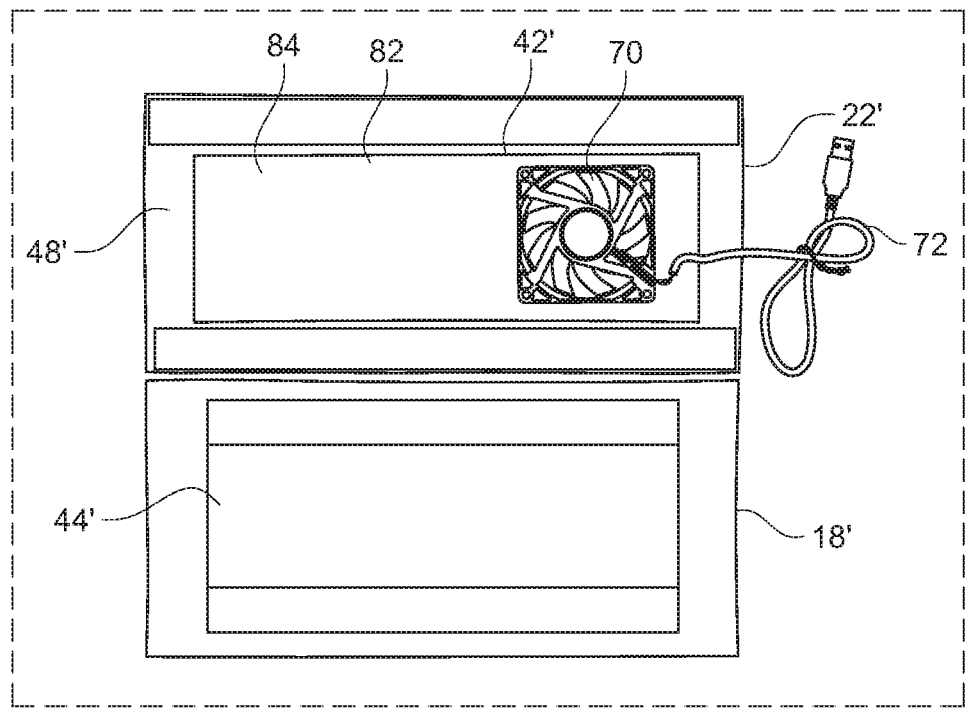
FIG. 17E is a view of the base insert in the base.
Figure 17F:
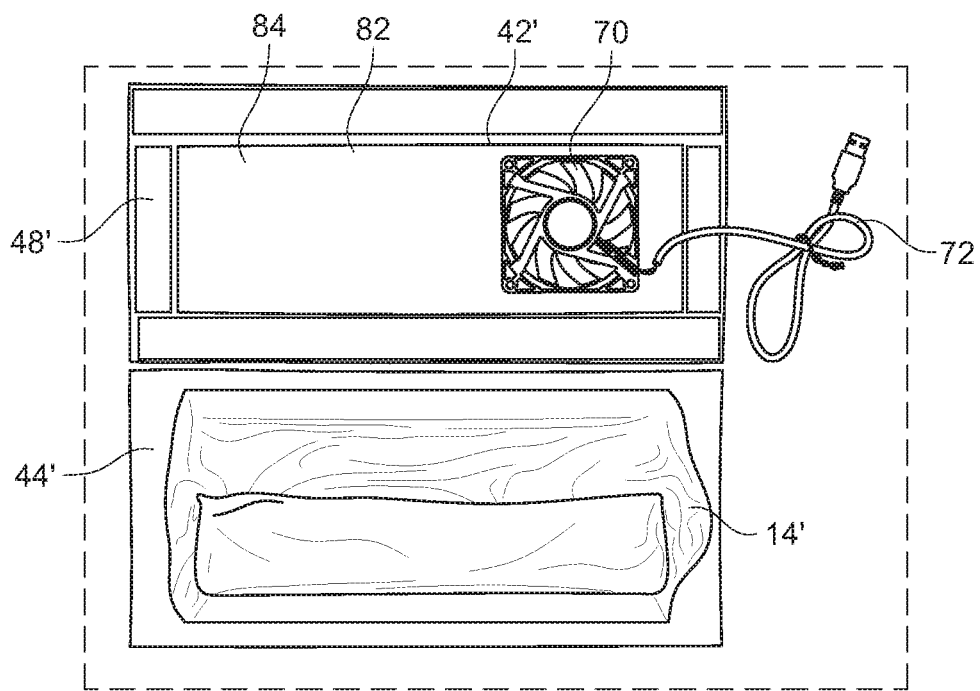
FIG. 17F is a view of the inflatable body in the base.
Figure 17G:
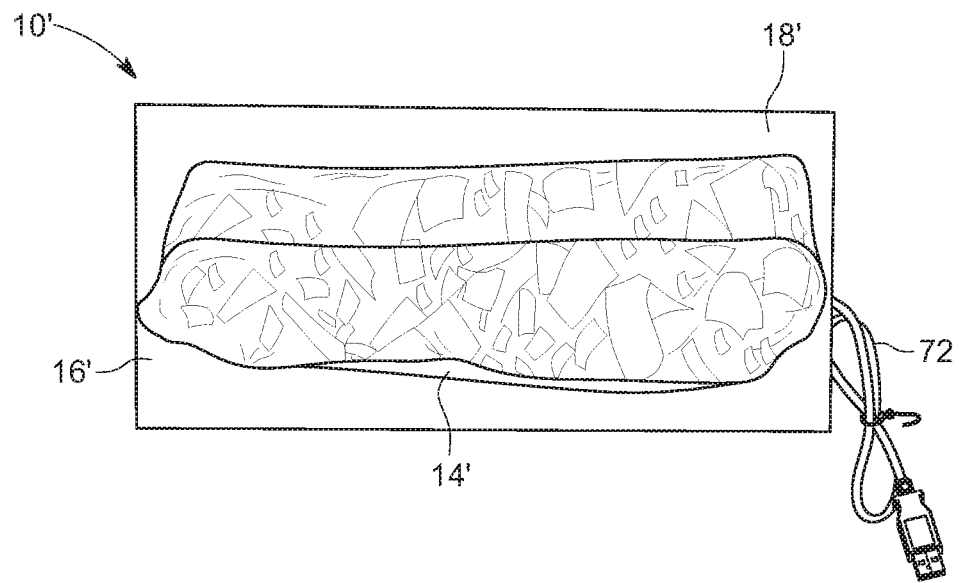
FIG. 17G is a top view of an assembled vent balloon with power cord.

The distal side 86 of the base insert 84 is operably attached and adhered to the inner side 48' of the base 16' covering the distal facing cutouts 42', such that the vent hole 76 of the base insert 84 fits within one of the distal facing cutouts 42' (FIG. 17E). The inflatable body 14' is secured over the proximal facing cutout 44' of the base 16' as described above. FIG. 17G shows a top view of the completed vent balloon 10' with the inflatable body 14' in a folded position, when the distal side 22' is folded to meet the proximal side 18' as described above.

Figure 18A:
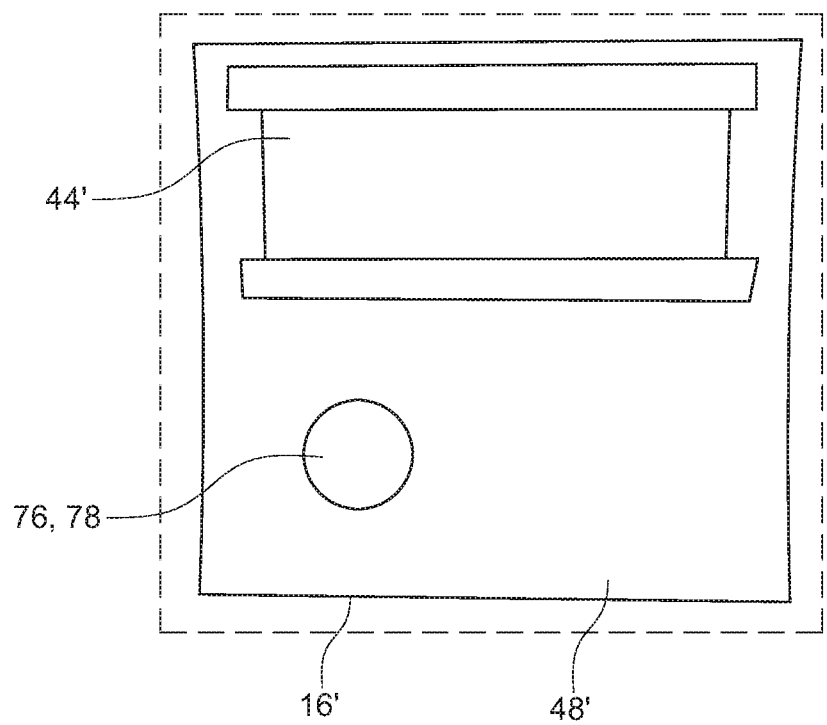
FIG. 18A is an inner view of a base with a circular vent hole.
Figure 18B:
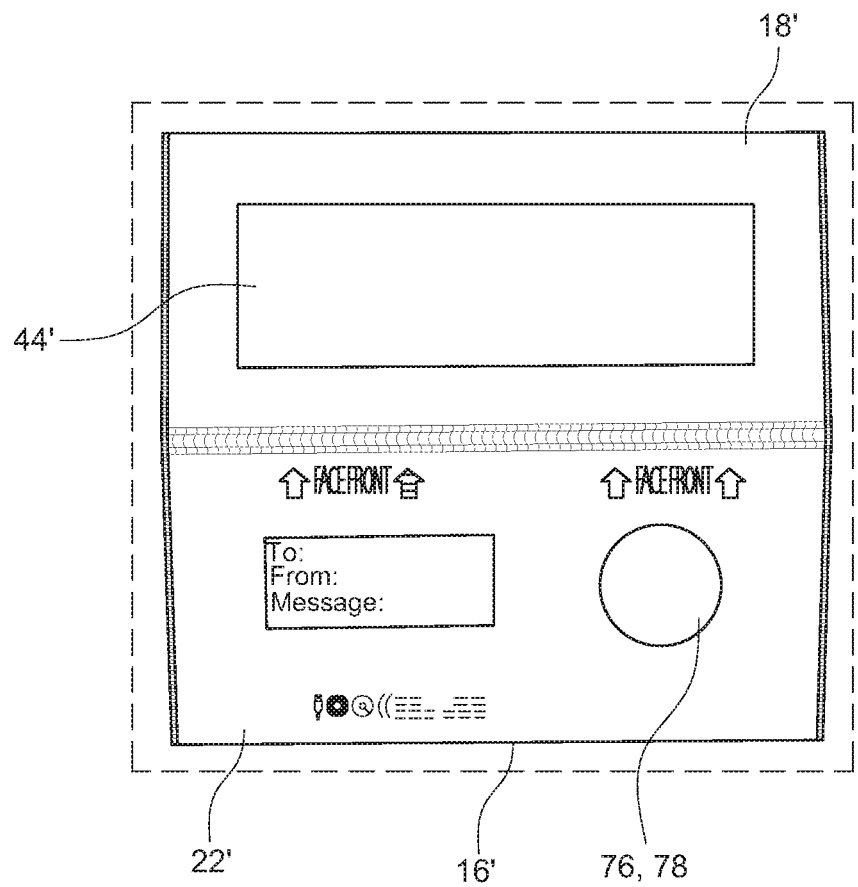
FIG. 18B is a view of a distal and proximal side of the base.
Figure 18C:
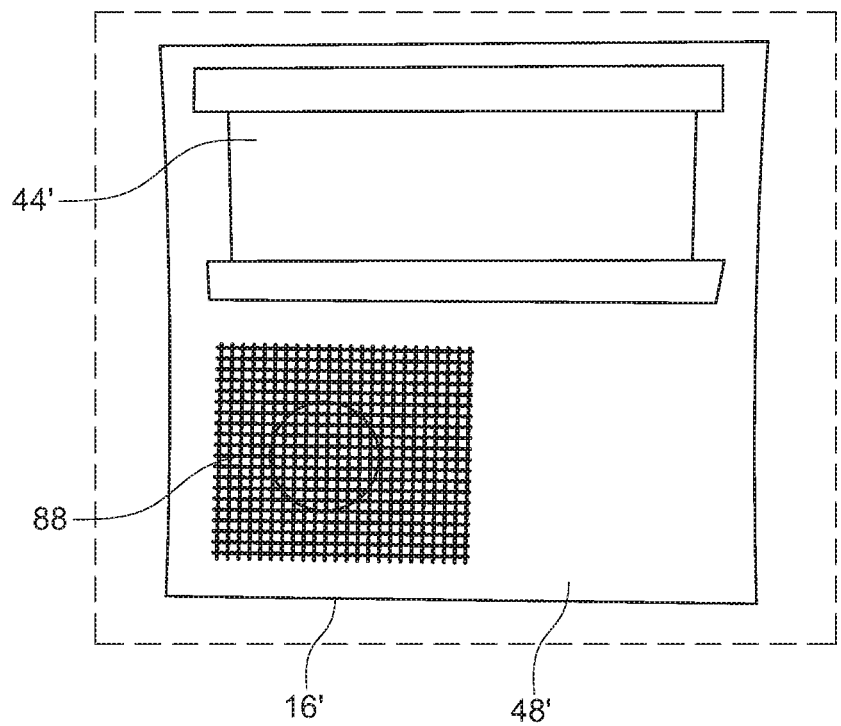
FIG. 18C is a view of the base with a mesh screen over the vent hole.
Figure 18D:
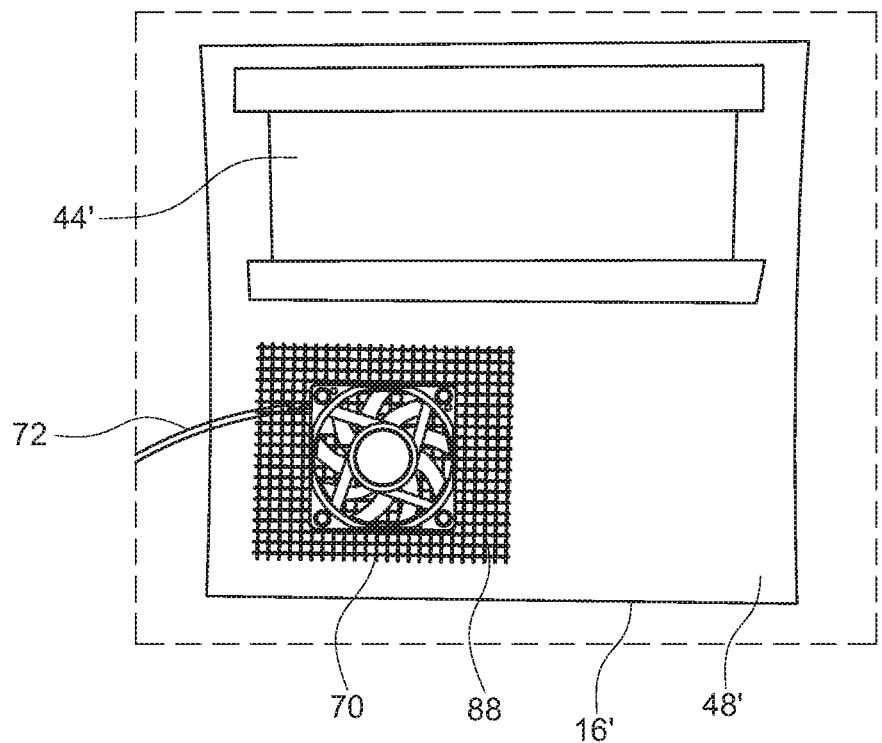
FIG. 18D is a view of the base with a fan attached to the mesh screen.
Figure 18E:
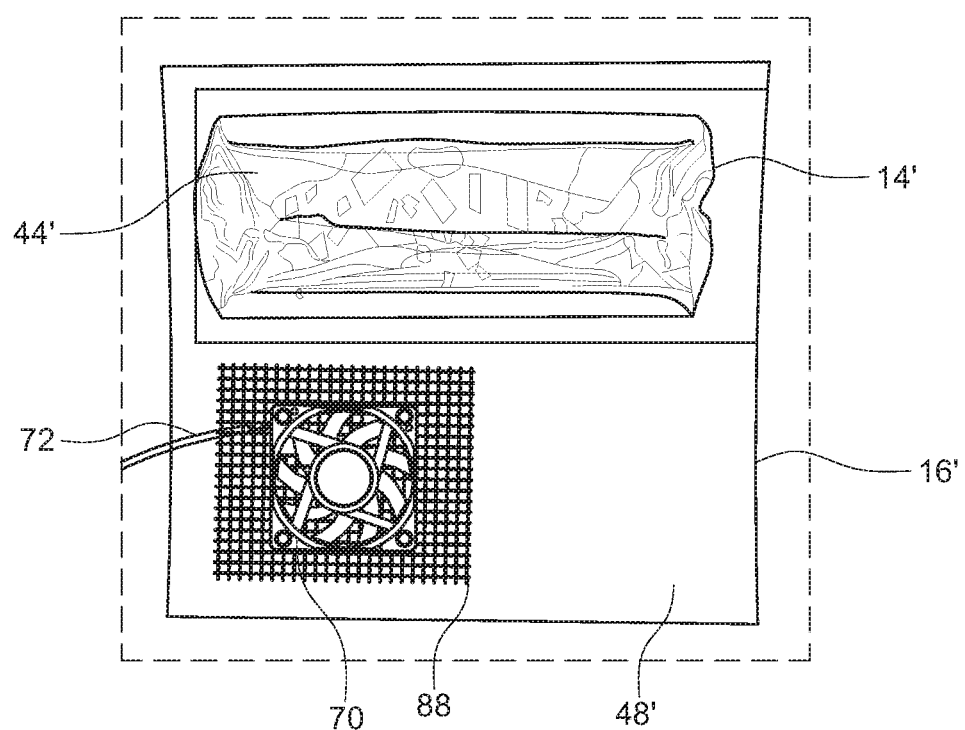
FIG. 18E is a view of the base with an inflatable body attached.
Figure 19A:
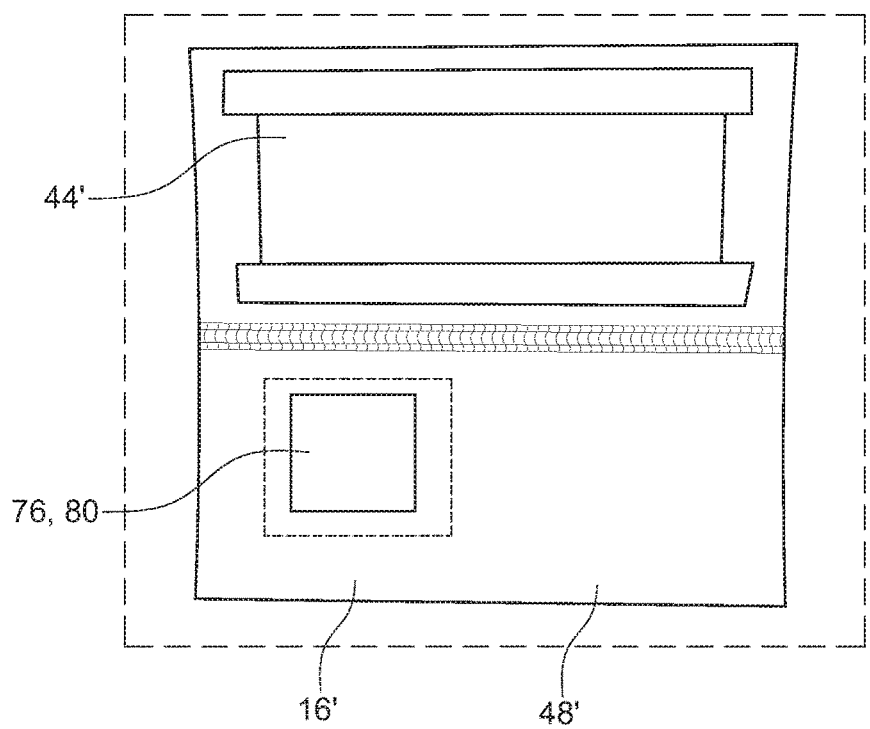
FIG. 19A is an inner view of a base with a square vent hole.
Figure 19B:
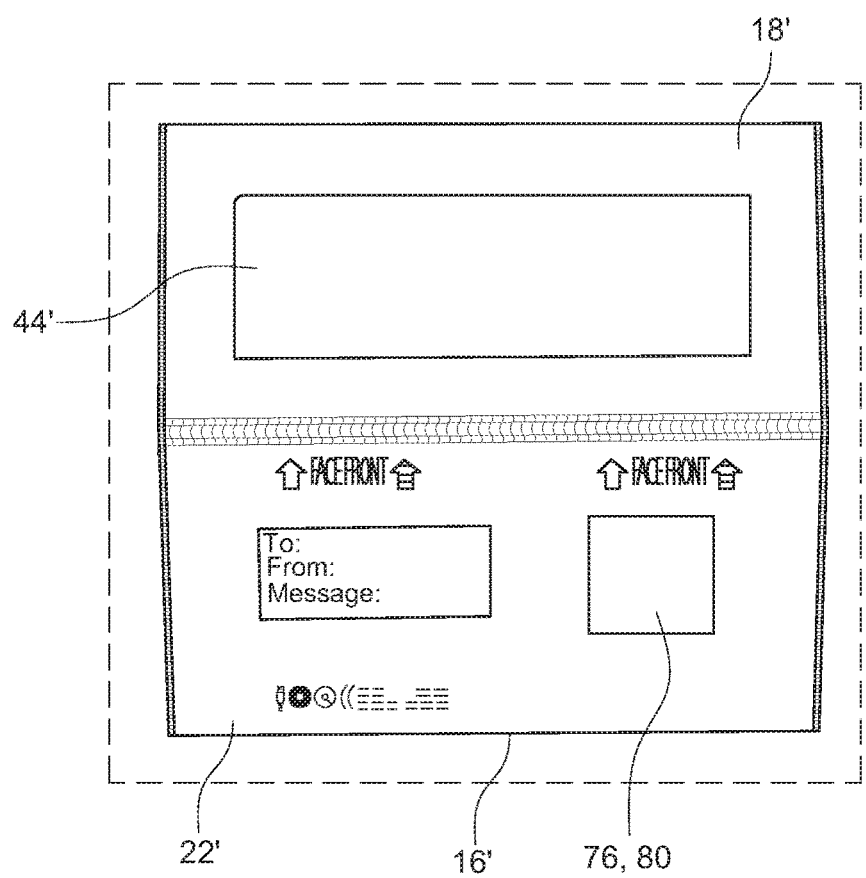
FIG. 19B is a view of a distal and proximal side of the base.

As in FIG. 16B-16C, FIGS. 18A-18E, and FIGS. 19A-19B, the base 16' itself can include the vent hole 76 instead of the distal facing cutouts 42'. FIG. 18A shows a view of the inner side 48' and FIG. 18B shows a view of the proximal side 18' and distal side 22' of the base 16', with circular shaped 78 vent hole 76. FIG. 19A shows a view of the inner side 48' and FIG. 19B shows a view of the proximal side 18' and distal side 22' of the base 16', with square shaped 80 vent hole 76. The mesh screen 88 can be adhered over the vent hole 76 on the inner side 48' of the base 16', as shown in FIG. 18C. Next, the fan 70 can be adhered on top of the mesh screen 88 over the vent hole 76 (FIG. 18D). The distal side 22' is then folded to meet the proximal side 18' as described above, and resulting in a completed vent balloon 10' as in FIG. 17G.

Figure 20:
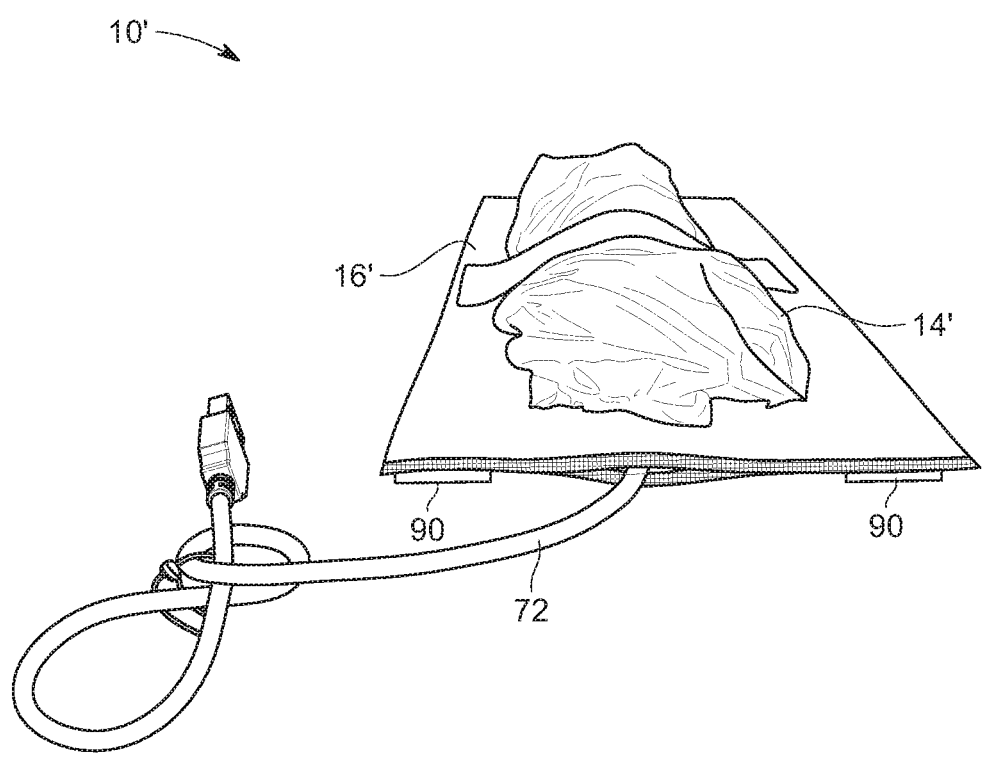
FIG. 20 is a side perspective view of a base with pads.

The base 16' can include multiple pads 90 adhered to the distal side 22' with adhesive or any other adhering mechanism in order to raise the distal side 22' from the flat surface that it rests on, as shown in FIG. 20. The pads 90 can be adhered at any desired place on the distal side 22'. This is critical for air flow into the base 16' via the fan 70 drawing air into the vent hole 76. The size of the pads 90 can be ¼" thick or more, and can be made of felt, foam, or any other suitable material. The pads can further include any suitable removable adhesive to adhere the base 16' to a flat surface, such as the removable adhesive 20 described above and protective strips 21' to protect the removable adhesive until use.

Figure 21A:
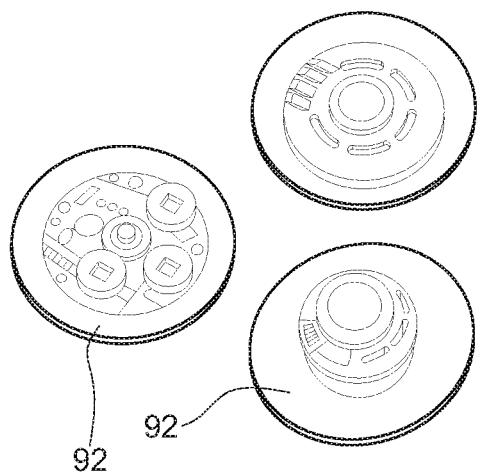
FIG. 21A is a depiction of sound modules.
Figure 21B:
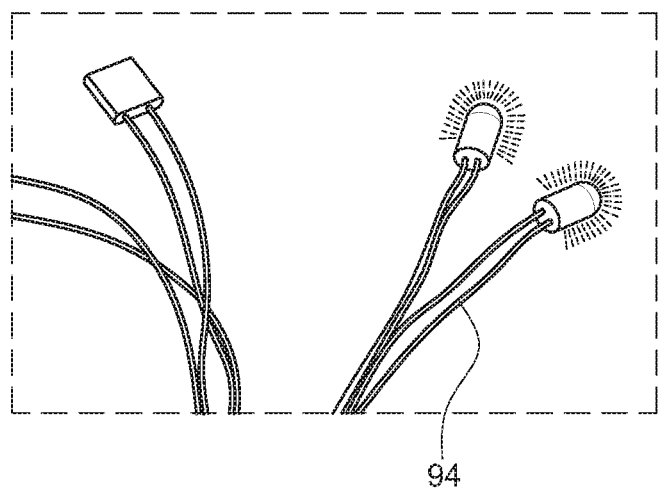
FIG. 21B is a depiction of light modules.
Figure 22A:
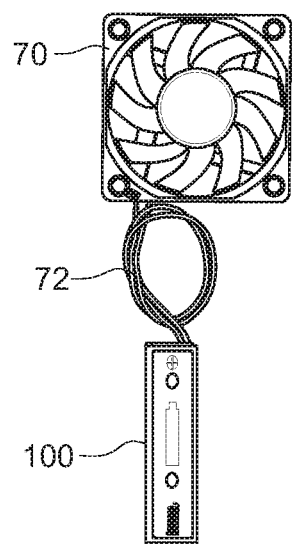
FIG. 22A is a top view of a fan with a battery.
Figure 22B:
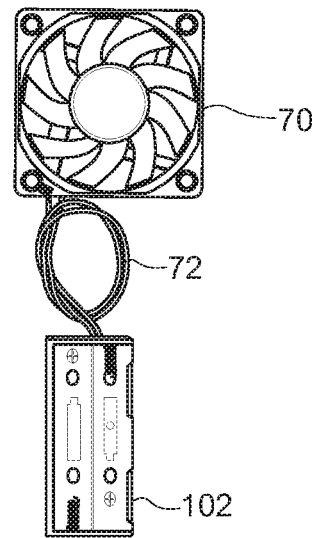
FIG. 22B is a top view of a fan with a battery pack.
Figure 22C:
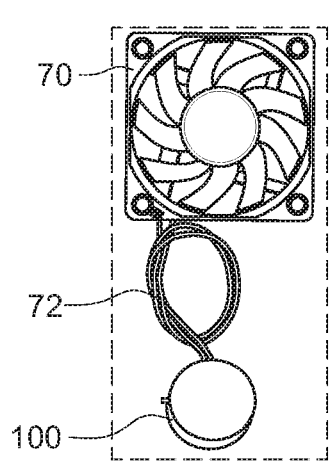
FIG. 22C is a top view of a fan with a battery.
Figure 22D:
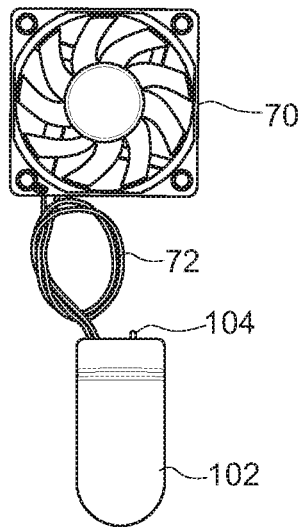
FIG. 22D is a top view of a fan with a battery pack.

The vent balloon 10' can further include LED flash sound modules 92 and/or LED flash light modules 94 attached any suitable place within the base 16' that are also powered by the power cord 72, shown in FIGS. 21A-21B. These modules 92 and 94 can be activated when the power cord 72 is plugged into a power source 74. The scent mechanism 36 can also be used with the power cord 72 to be activated when plugged into a power source 74. Any combination of these modules can be used.

The present invention also provides for a method of using the vent balloon 10' on a flat surface, by placing the inflatable body 14' through the base 16' on a flat surface, powering the vent balloon 10', activating the fan 70 in the base 16', flowing air through the inflatable body 14' with the fan, and inflating the inflatable body 14'. More specifically, when present, the pads 90 on the distal side 22' of the base 16' can be removably adhered to a flat surface such as a tabletop or desk after removing protective strips 21'. The vent balloon 10' can be powered by plugging the power cord 72 into a power source 74 or by actuating an off/off switch 104 of a battery 100 or battery pack 102. Once the vent balloon 10' is inflated, the inflatable body 14' stands upright and the design 30' is displayed and visible. A portion of the air also flows through vents 28' out of the inflatable body 14' such that the vent balloon 10' maintains its inflated shape without lifting off of the flat surface. The vent balloon 10' can include any of the features described above, and can use a lay-flat polyethylene bag or gusseted polyethylene bag, and include any design 30'. The vent balloon 10' can also be initially folded, obscuring or hiding the design 30', and once the fan 70 is activated, the inflatable body 14' unfolds and inflates to reveal the design 30', especially to reveal a surprise message. Any scent mechanism 36, LED flash sound modules 92, and/or LED flash light modules 94 can also be actuated when the power cord 72 is plugged in. When it is desired to stop using the vent balloon 10', the power cord 72 can be unplugged from the power source 74.

The step of making the base 16' of molded plastic 110, as in FIG. 23, eliminates the need for glue or adhesive within the base 16' as above to manufacture. Base pads 90 described below can further be eliminated if desired as the base 16' can be heavy enough to maintain its position when the inflatable body 14 is inflated. A molded plastic 110 allows for high volume assembly and a more rigid structure that will not be damaged during shipping or use. The base 16' can include a molded slot 112 for fan 70 to sit in and be secured by clips 114. Otherwise a molded plastic 110 base 16' can have any of the other properties as described above. The molded plastic base 110 can also include a cord slot 116 for maintaining position of power cord 72. The molded plastic base 110 can be manufactured as two pieces, having a top side 118 for securing the inflatable body 14' and a bottom side 120 (containing the molded slot 112). The top side 118 and bottom side 120 can be secured by any suitable mechanism, such as by engaging a plurality of pins 122 through a plurality of pin slots 124 (shown in FIG. 24).

Figure 25A:
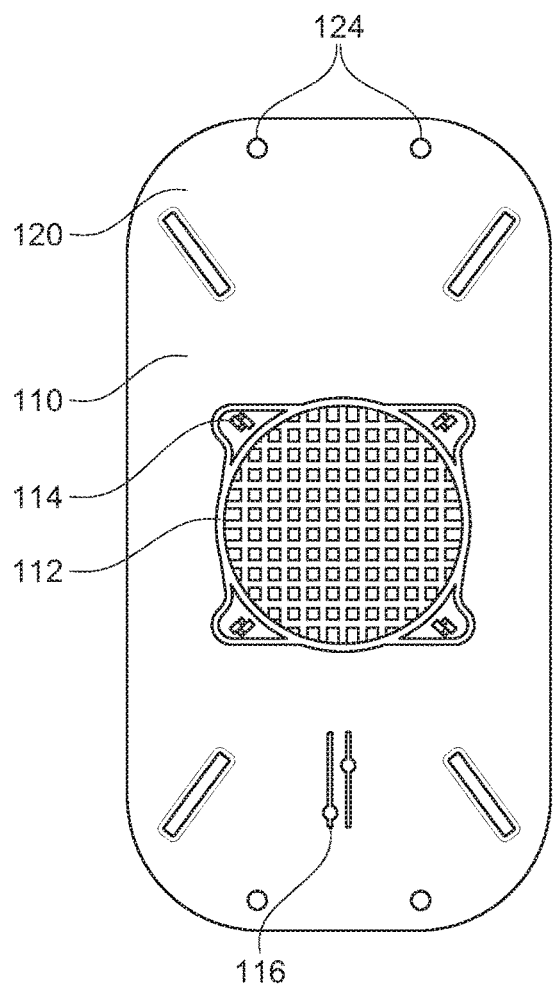
FIG. 25A is a top view of a molded plastic base.
Figure 25B:
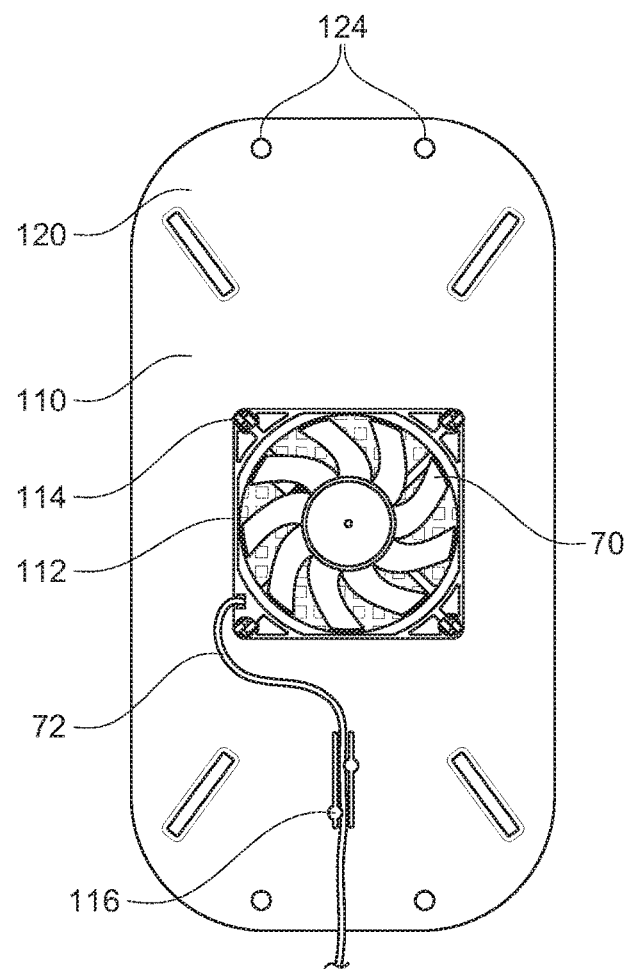
FIG. 25B is a top view of a molded plastic base with a fan and power cord attached.
Figure 25D:
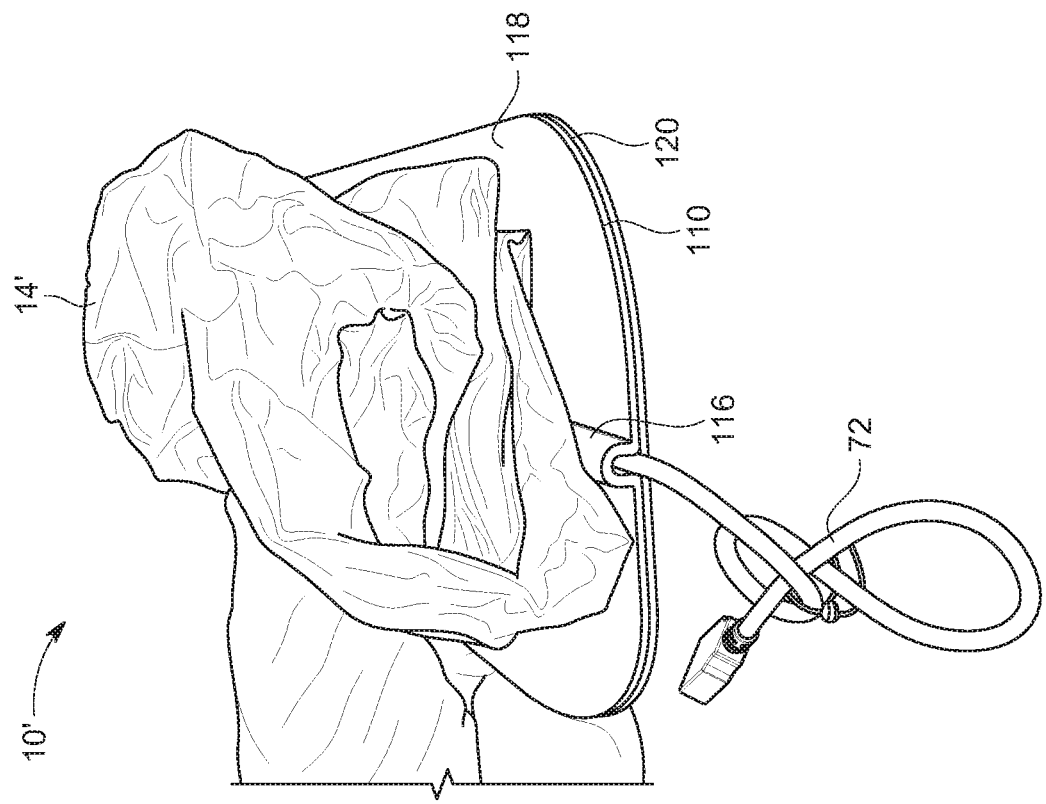
FIG. 25D is a top perspective view of an assembled vent balloon with a molded plastic base.
Figure 25C:
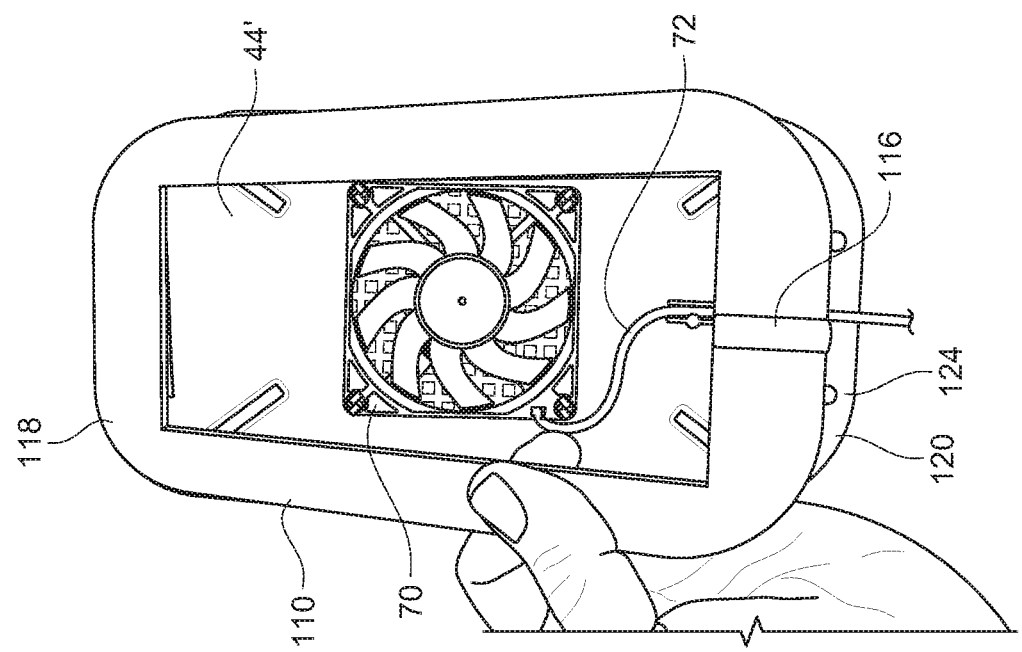
FIG. 25C is a top view of a molded plastic base with a top side and bottom side.

FIGS. 25A-25D show different stages of assembly of the vent balloon 10' with a molded plastic base 110. FIG. 25A shows the bottom side 120 of the molded plastic base 110 at the start of assembly and FIG. 25B shows the bottom side 120 with a fan 70 attached within the molded slot 120 and secured by clips 114 and power cord 72 secured in cord slot 116. FIG. 25C shows the position of the top side 118 of the molded plastic base 110 over the bottom side 120. FIG. 25D shows the completed vent balloon 10' including the inflatable body 14'.

The present invention preferably provides for a vent balloon 10', including an inflatable body 14, 14' operatively attached to a molded plastic base 110 on a proximal side 18', wherein the inflatable body 14, 14' is inflated by a mechanism of an air vent 12 or a fan 70 operatively attached to the molded plastic base 110, and including a scent mechanism 36 operatively attached to the molded plastic base 110 for dispersing scent in a room that relates to a design 30, 30' on the inflatable body 14, 14'.

The present invention also provides for a method of using a vent balloon 10' by flowing air through the inflatable body 14, 14' of the vent balloon 10' through a molded plastic base 110, wherein the air comes from a source of an air vent 12 or a fan 70 operatively attached to the molded plastic base 110, inflating the inflatable body 14, 14', and flowing air over at least one scent mechanism 36 operatively attached to the molded plastic base 110 that relates to a design 30, 30' on the inflatable body 14, 14' and releasing scent into the air.

There are several advantages to the vent balloon 10 of the present invention. When the base 16 is made of plastic, this allows for a UL rating for product liability to be obtained during use over a hot air vent 12. Plastic is also more aesthetically pleasing to the consumer. A flexible plastic base 16 allows the vent balloon 10 to be mailed to the consumer without damage if bent during mail processing and delivery, and also allows for a reduced mailing cost versus an inflatable base due to the size. The vent balloon 10 being lightweight also allows for a low mailing cost.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:
1. A vent balloon, comprising:
an inflatable body depicting a design and having a first end, an open second end and at least one vent;
a flat molded plastic base having an upper panel coupled to a lower panel by an engagement of respective pins and pin slots on said upper and lower panels, said upper panel having an exterior surface, an interior surface and a central aperture and said lower panel having an interior surface and an exterior surface with said exte- rior surface of said lower panel including an adhesive with removable protective strips covering said adhesive; and a scent mechanism operatively attached to said molded plastic base and having a scent related to said design depicted by said inflatable body;

wherein said inflatable body is attached to said molded plastic base so as to extend through said central aperture with said open second end of said inflatable body positioned between said upper and lower panels and attached by an adhesive to said interior surface of said upper panel to form an air tight seal with said molded plastic base; and wherein air introduced into said vent balloon by a mechanism selected from the group consisting of an air vent and a fan operatively attached to said molded plastic base inflates said inflatable body such that air and scent are dispersed through said at least one vent.

2. The vent balloon of claim 1, wherein said inflatable body is made of a material chosen from the group consisting of polyethylene, MYLAR®, and foil.

3. The vent balloon of claim 1, wherein said inflatable body is a polyethylene bag chosen from the group consisting of a lay-flat polyethylene bag and a gusseted polyethylene bag.

4. The vent balloon of claim 1, wherein said inflatable body design is chosen from the group consisting of a holiday greeting, congratulations, a personal message, cartoon characters, general celebratory designs, and promotional advertisements.

5. The vent balloon of claim 1, wherein said first end of the inflatable body is closed.

6. The vent balloon of claim 1, wherein said fan is powered with a power cord chosen from the group consisting of a USB power cord, a lightning power cord, an AC/DC power cord, and a cord that connects to a battery.

7. The vent balloon of claim 6, further including a mechanism chosen from the group consisting of an LED flash sound module, an LED flash light module, and combinations thereof, operably attached to said molded plastic base and powered by said power cord.

8. The vent balloon of claim 6, wherein said molded plastic base includes a molded slot in which said fan sits, clips for securing said fan within said molded slot, and a cord slot for securing said power cord.

9. The vent balloon of claim 1, wherein said molded plastic base is rectangular and fits over a standard air vent.

10. A method of using a vent balloon, including the steps of:

providing a vent balloon having:

an inflatable body depicting a design and having a first end, an open second end and at least one vent;

a flat molded plastic base having an upper panel coupled to a lower panel by an engagement of respective pins and pin slots on the upper and lower panels, the upper panel having an exterior surface, an interior surface and a central aperture and the lower panel having an interior surface and an exterior surface with the exterior surface of the lower panel including an adhesive with removable protective strips covering the adhesive; and a scent mechanism operatively attached to the molded plastic base and having a scent related to the design depicted by the inflatable body;

wherein the inflatable body is attached to the molded plastic base so as to extend through the central aperture with the open second end of the inflatable body positioned between the upper and lower panels and attached by an adhesive to the interior surface of the upper panel to form an air tight seal with the molded plastic base; and introducing air from a source selected from the group consisting of an air vent and a fan operatively attached to the base into the vent balloon through the base to inflate the inflatable body and cause air to flow over the scent mechanism to disperse the scent through the at least one vent.

11. The method of claim 10, further including, before introducing air from a source, the step of removably adhering the exterior surface of the lower panel to the air vent.

12. The method of claim 10, wherein inflating the inflatable body includes causing the inflatable body to stand upright and display the design.

13. The method of claim 11, further including the step of flowing a portion of the air in the inflatable body through the at least one vent in the inflatable body such that the vent balloon maintains an inflated shape without lifting off of the air vent.

14. The method of claim 10, wherein the inflatable body is a polyethylene bag chosen from the group consisting of a lay-flat polyethylene bag and a gusseted polyethylene bag.

15. The method of claim 10, further including the steps of supplying power to activate the fan by a step chosen from the group consisting of plugging a power cord into a power source and actuating an on/off switch.

16. The method of claim 10, further including the step of actuating a mechanism chosen from the group consisting of an LED flash sound module, an LED flash light module, and combinations thereof.

* * * * *